United States Patent
Teles et al.

(10) Patent No.: US 8,785,670 B2
(45) Date of Patent: Jul. 22, 2014

(54) PROCESS FOR THE PRODUCTION OF PROPYLENE OXIDE

(75) Inventors: Joaquim Henrique Teles, Waldsee (DE); Kai Gumlich, Mannheim (DE); Peter Bassler, Viernheim (DE); Christian Bartosch, Mannheim (DE); Philip Kampe, Lorsch (DE); Hans-Georg Goebbel, Kallstadt (DE); Ulrich Mueller, Neustadt (DE); Richard Jacubinas, Bloomfield, NJ (US)

(73) Assignees: BASF SE, Ludwigshafen (DE); The Dow Chemical Company, Midland, MI (US)

( * ) Notice: Subject to any disclaimer, the term of this patent is extended or adjusted under 35 U.S.C. 154(b) by 162 days.

(21) Appl. No.: 13/312,222

(22) Filed: Dec. 6, 2011

(65) Prior Publication Data

US 2012/0142950 A1 Jun. 7, 2012

Related U.S. Application Data

(60) Provisional application No. 61/420,335, filed on Dec. 7, 2010.

(51) Int. Cl.
*C07D 301/12* (2006.01)
(52) U.S. Cl.
USPC ........................................................ 549/531
(58) Field of Classification Search
USPC ........................................................ 549/531
See application file for complete search history.

(56) References Cited

U.S. PATENT DOCUMENTS

| | | | |
|---|---|---|---|
| 4,824,976 A | 4/1989 | Clerici et al. | |
| 4,937,216 A | 6/1990 | Clerici et al. | |
| 5,646,314 A * | 7/1997 | Crocco et al. | 549/531 |
| 5,675,026 A | 10/1997 | Thiele | |
| 6,429,322 B1 | 8/2002 | Catinat et al. | |
| 7,594,979 B2 * | 9/2009 | Patrascu et al. | 203/1 |
| 2002/0004606 A1 | 1/2002 | Thiele | |
| 2003/0162983 A1 | 8/2003 | Strebelle et al. | |

FOREIGN PATENT DOCUMENTS

| | | |
|---|---|---|
| EP | 0 230 949 A2 | 8/1987 |
| EP | 0 712 852 A1 | 5/1996 |
| EP | 0 757 043 A1 | 2/1997 |
| EP | EP 1 085 017 A1 | 3/2001 |
| EP | EP 1 122 249 A1 | 8/2001 |
| WO | WO 99/48882 | 9/1999 |
| WO | WO 2004/029032 A1 | 4/2004 |
| WO | WO 2005/103024 A1 | 11/2005 |
| WO | WO 2007/074101 A1 | 7/2007 |
| WO | WO 2010/130610 A1 | 11/2010 |

OTHER PUBLICATIONS

International Search Report issued May 2, 2012 in patent application No. PCT/EP2011/071955 filed Dec. 6, 2011.

(Continued)

*Primary Examiner* — T. Victor Oh
(74) *Attorney, Agent, or Firm* — Oblon, Spivak, McClelland, Maier & Neustadt, L.L.P.

(57) ABSTRACT

A continuous process for the production of propylene oxide comprising reacting propene with hydrogen peroxide in methanolic solution in the presence of a titanium silicalite-1 catalyst to obtain propylene oxide, wherein a reaction feed comprising propene, methanol and hydrogen peroxide is introduced into a reactor, said reaction feed containing potassium cations and phosphorus in the form of anions of at least one phosphorus oxyacid.

21 Claims, 1 Drawing Sheet

(56) References Cited

OTHER PUBLICATIONS

Mario G. Clerici, et al., "Epoxidation of Lower Olefins with Hydrogen Peroxide and Titanium Silicalite", Journal of Catalysis, vol. 140, 1993, pp. 71-83.

Gustaaf Goor, et al., "High-Performance Fibers to Imidazole and Derivatives", Ullmann's Encyclopedia of Industrial Chemistry, vol. A13, Fifth, Completely Revised Edition, 1989, pp, 443-466.

"Poly(Vinyl Esters) to Reduction", Ullmann's Encyclopedia of Industrial Chemistry, vol. A22, Fifth, Completely Revised Edition, 1993, p. 214.

* cited by examiner

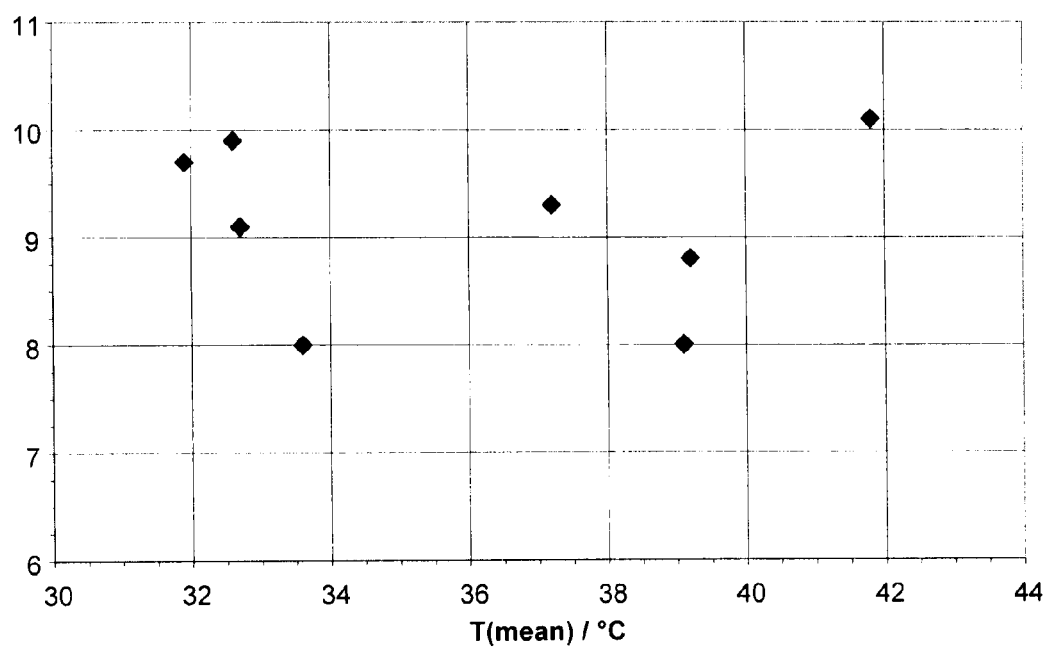

PROCESS FOR THE PRODUCTION OF PROPYLENE OXIDE

The present invention relates to a continuous process for the preparation of propylene oxide. According to the inventive process, propene is reacted with hydrogen peroxide in methanolic solution in the presence of a titanium silicalite-1 catalyst to obtain propylene oxide. The reaction feed which is introduced in the at least one reactor in which the inventive continuous epoxidation process is carried out comprises propene, methanol and hydrogen peroxide. Further, this reaction feed comprises a specific amount of potassium cations and additionally phosphorus in the form of anions of at least one phosphorus oxyacid.

Conversion and selectivity of epoxidation reactions can be influenced, for example, via the temperature of the epoxidation reaction, the pH of the epoxidation reaction mixture, and/or addition of one or more compounds to the reaction mixture other than the reactants propene and hydrogen peroxide.

Clerici et al. (J. Catal. 140 (1993) pp. 71-83) describe the effect of adding certain compounds to the epoxidation of propene and the olefins with hydrogen peroxide in methanol as solvent and in the presence of titanium silicalite-1 as catalyst. In this scientific paper, the effects of various basic, neutral or acidic additives were examined. However, no clear and unequivocal connection between the chemical nature of the additive and the observed effect on conversion and selectivity was found. It was said that small amounts of alkali metal hydroxides and alkali metal acetates have positive influence on the selectivity although the addition of lithium acetate completely inhibits the oxidation of 1-butene.

EP 0 230 949 A2 describes a process for the preparation of propylene oxide by epoxidizing propene with hydrogen peroxide in the presence of titanium silicalite-1 as catalyst wherein prior to or during the reaction, the acidity of the catalyst used is suitably neutralized by a neutralizing agent. Neutralization prior to the reaction is achieved by using suitable silylating agents. However, this process has the disadvantage in that the catalyst has to be subjected to a silylating reaction after each regeneration cycle. According to EP 0 230 949 A2, neutralization during the reaction can be achieved by adding strong or weak basic chemical compounds. For example, sodium hydroxide or potassium hydroxide is mentioned as strong bases. As weak bases, ammonium hydroxide, sodium carbonate, sodium hydrogen carbonate, sodium hydrogen phosphate and the respective potassium and lithium salts, as well as alkali metal salts and earth alkaline metal salts of organic acids with one to ten carbon atoms and/or alkali metal alcoholate or earth alkaline metal alcoholates with one to ten carbon atoms are mentioned. According to this document, these additives can be used in a very broad concentration range. For example, the hydrogen peroxide solution used for epoxidation reaction can be admixed with a base in the amount of 0.0001 and 0.1 wt.-%. According to this document, no special effects are shown for specific additives. The main aspect of this document is the neutralization of the catalyst, which can be achieved with every suitable basic additive.

EP 0 712 852 A1 also describes a process for the epoxidation of propene with hydrogen peroxide in the presence of titanium silicalite-1 as catalyst. According to this document, addition of non-basic salts can lead to improved selectivities wherein these non-basic salts are added to the hydrogen peroxide solution used. According to this document, non-basic salts are salts which, at a concentration of 0.1 mol/l in water at 25° C. have a pH of less than 8 but more than 4. Explicitly mentioned are ammonium, alkali metal, and earth alkaline metal salts wherein the anions are, for example, halides, nitrates, sulphates, formates, acetates, hydrogen carbonates, or anions of oxyacids which contain phosphorus, arsenic, antimony or tin. Also in this context, the additives can be added in very broad concentration ranges wherein between 0.00001 and 0.02 mol/l are suggested. Further, this document is silent on any special effects which may be achieved by using specific salts.

EP 0 757 043 A1 also describes such epoxidation process for the preparation of propylene oxide using hydrogen peroxide in the presence of titanium silicalite-1 as catalyst. According to this document, prior to, or during the reaction, neutral or acidic salts are employed. Explicitly mentioned salts contain cations from the group consisting of lithium, sodium, potassium, ammonium, $RNH_3^+$ or $R_2NH_2^+$ with anions from the group consisting of sulphate, nitrate, chlorate, chloride, or dihydrogen phosphate. The concentration of such salt can be in the range of between 0.0001 and 1 mol/l. Contrary to the documents cited above, it is disclosed that using basic salts may lead to higher catalytical activities. However, using these basic salts may, at the same time, lead to a decreased selectivity.

WO 99/48882 A1 also describes a process for the epoxidation of propene with hydrogen peroxide in the presence of titanium silicalite-1 as catalyst wherein the pH of the reaction mixture is kept between 4.8 and 6.5. In order to adjust the pH in this range, it is disclosed that basic compounds have to be added. As especially preferred base, sodium acetate is mentioned. According to this document, it is not important which specific basic additives are employed. Quite to the contrary, it is described that irrespective of the nature of the added base, superior results are achieved if the pH of the reaction mixture is kept in said specific range.

WO 2004/029032 A1 relates to a continuous process for the epoxidation of olefins using a heterogeneous catalyst for promoting the epoxidation reaction, in particular titanium silicalite-1. In order to prevent deactivation of the catalyst, it is taught that the aqueous reaction mixture should comprise an olefin, hydrogen peroxide, less than 100 wppm (weight-ppm) of alkali metals, earth alkali metals, both irrespective whether in ionic or complex form, bases or cations of bases having a $pK_B$ of less than 4.5, or combinations thereof; and at least 100 wppm of bases or cations of bases having a $pK_B$ of at least 4.5 or combinations thereof, whereby the wppm are based on the total weight of hydrogen peroxide in the reaction mixture. According to a preferred embodiment, the reaction mixture should further comprise at least 100 wppm anions or compounds that can dissociate to form anions in total based on the weight of hydrogen peroxide wherein such anions, preferably present in the usual stabilizing amounts, are preferably any kind of oxophosphorous anions like orthophosphate, hydrogen phosphate, hydrogen phosphate, pyrophosphate, nitrate. As to these stabilizing anions, or compounds that can dissociate in the hydrogen peroxide solution to produce these stabilizing anions, WO 2004/029032 A1 discloses that they should be present in an amount of at most 1000 wppm, preferably 100-1000 wppm, more preferably 200-800 wppm, most preferably 200-600 wppm, based on the weight of hydrogen peroxide. Cations present in compounds employed according to WO 2004/029032 A1 are sodium and lithium, disclosed in the inventive examples.

EP 1 085 017 A1 also describes a process for the epoxidation of propene with hydrogen peroxide in the presence of titanium silicalite-1 as catalyst. According to this document, it is important to keep the pH of the hydrogen peroxide solution employed in the range of from 4 to 6.5, or the pH of the reaction medium in the range of from 5 to 9.5. In order to achieve the desired pH, various bases are mentioned. For example, alkali metal hydroxides, alkali metal carbonates, alkali metal hydrogen carbonates, alkali metal phosphates, alkali metal carboxylates, and ammonia are disclosed. From this document, the skilled person learns that it is not the specific chemical nature of the bases used, but solely the pH which leads to the desired effect.

It was an object of the present invention to provide an improved process for the epoxidation of propene with hydrogen peroxide in the presence of titanium silicalite-1 as catalyst providing for a low selectivity with respect to by-products and side-products of the epoxidation reaction while, at the same time, allowing for very high conversion rates with respect to the starting material hydrogen peroxide.

Surprisingly, it was found that this problem can be solved if in the continuous epoxidation of propene in methanolic solution in the presence of titanium silicalite-1 as catalyst, a specific alkali metal cation is present in the reaction mixture in a specific and narrow concentration range relative to hydrogen peroxide, wherein the reaction mixture further contains phosphorus in the form of anions of at least one phosphorus oxyacid.

Therefore, the present invention relates to a continuous process for the production of propylene oxide comprising reacting propene with hydrogen peroxide in methanolic solution in the presence of a titanium silicalite-1 catalyst to obtain propylene oxide, wherein a reaction feed comprising propene, methanol and hydrogen peroxide is introduced into a reactor, said reaction feed containing potassium cations ($K^+$) in an amount of from 110 to 190 micromol, relative to 1 mol hydrogen peroxide contained in the reaction feed, and further containing phosphorus (P) in the form of anions of at least one phosphorus oxyacid.

The term "anions of a phosphorus oxyacid" as used in the context of the present invention relates to an anion, or a mixture of two or more anions which can be simultaneously present in equilibrium, of every conceivable phosphorus oxyacid. By way of example, peroxophosphoric acid ($H_3PO_5$), phosphoric acid ($H_3PO_4$), phosphonic acid ($H_3PO_3$), phosphinic acid ($H_3PO_2$), hypodiphosphonic acid ($H_4P_2O_4$), diphosphonic acid ($H_4P_2O_5$), hypodiphosphoric acid ($H_4P_2O_6$), diphosphoric acid ($H_4P_2O_7$), peroxodiphosphoric acid ($H_4P_2O_5$), triphosphoric acid ($H_5P_3O_{10}$) may be mentioned by way of example. Preferred anions are anions derived from phosphoric acid ($H_3PO_4$) and diphosphoric acid ($H_4P_2O_7$). Further, the term "phosphorus oxyacid" comprises organic phosphonic acids of formula (R—P(=O)(OH)$_2$ such as etidronic acid $CH_3C(OH)(P(=O)(OH)_2)_2$.

Reaction Feed

According to the present invention, said potassium cations and said anions of at least one phosphorus oxyacid are contained in a reaction feed. The term "reaction feed" as used in this context of the present invention relates to a feed containing the complete amount of propene, the complete amount of hydrogen peroxide, and the complete amount of methanol introduced in the reactor as starting materials. This reaction feed can be introduced into the reactor as one single feed stream or as individual feed streams such as, for example, a feed stream containing methanol and hydrogen peroxide and a feed stream containing propene, or a feed stream containing methanol and propene and a feed stream containing hydrogen peroxide, or a feed stream containing methanol and a feed stream containing propene and a feed stream containing hydrogen peroxide. If more than one feed stream is employed, the individual feed streams are either mixed before they are introduced in the reactor or suitably mixed after having been introduced into the reactor.

According to a preferred embodiment of the present invention, at least three individual feed streams are used, at least one of which is the feed with which the methanol is introduced into the reactor, at least one of which is the feed with which the propene is introduced into the reactor, and at least one of which is the feed with which the hydrogen peroxide is introduced into the reactor. Therefore, the overall methanol feed can be comprised of one or more individual methanol feed streams, the overall propene feed can be comprised of one or more individual propene feed streams, and the overall hydrogen peroxide feed can be comprised of one or more individual hydrogen peroxide feed streams. These streams are suitable mixed, as described above.

Therefore, the present invention is directed to above-described process wherein the reaction feed is obtained from a hydrogen peroxide feed, a methanol feed, and a propene feed.

As far as the methanol feed is concerned, it may be comprised of a feed stream of fresh methanol and at least one methanol stream obtained in at least one downstream stage of the overall process for the production of propylene oxide. Such latter methanol stream is referred to hereinunder as "recycled methanol stream" or "recycled methanol feed stream". Further, the methanol feed may be comprised of a fresh methanol stream only, or be comprised of a recycled methanol stream only. Preferably, it is comprised of a mixture of a fresh methanol stream and a recycled methanol stream.

As far as the propene feed is concerned, it may be comprised of a feed stream of fresh propene and at least one propene stream obtained in at least one downstream stage of the overall process for the production of propylene oxide. Such latter propene stream is referred to hereinunder as "recycled propene stream" or "recycled propene feed stream". Further, the propene feed may be comprised of a fresh propene stream only. Preferably, it is comprised of a mixture of a fresh propene stream and a recycled propene stream.

Preferably, the individual streams are suitably mixed before they are introduced into the reactor. No specific order of mixing is required. Preferably, the individual streams, more preferably the fresh methanol stream, the recycled methanol stream, the fresh propene stream, the recycled propene stream, and the hydrogen peroxide stream, are mixed in a manner so that no solids are formed. The term "no solids" as used in this specific context of the present invention relates to solid contents of at most, preferably less than 0.2 weight-ppm based on the weight of the entire reaction feed. According to the present invention, it is further preferred to suitably mix the individual streams to obtain a reaction feed which comprises a liquid phase. Preferably, the individual streams are suitably mixed to obtain a reaction feed which consists of at least one liquid phase. Even more preferably, the individual streams are suitably mixed to obtain a reaction feed which consists of one liquid phase. Therefore, the present invention is directed to above-described process wherein the reaction feed when introduced into the reactor consists of one liquid phase.

Propene Feed

Generally, propene can be employed in the process of the present invention, in particular as fresh propene stream, as pure propene stream containing only minor amounts of impurities such as propane or the like. Preferably, the propene feed as described above contains at least 90 vol.-%, more preferably at least 95 vol.-% propene. Thus, propene qualities can be employed usually referred to as "chemical grade propene" or "polymer grade propene". Generally, propane is the main component comprised in propene of such qualities besides propene. The volume ratio of propene to propane of the propene feed stream preferably used according to the present invention is in the range of from 99.99:0.01 to 95:5. Therefore, the present invention is directed to above-described process, wherein the propene feed, in particular the fresh propene feed stream, additionally contains propane wherein the volume ratio of propene to propane is preferably in the range of from 99.99:0.01 to 95:5. More preferably, the propene feed, in particular the fresh propene feed stream, additionally contains propane wherein the volume ratio of propene to propane is in the range of from 99:1 to 95:5, more preferably from 97:3 to 95:5.

As described above, according to a preferred embodiment of the present invention, it is possible to separate propene which has not been reacted during the epoxidation reaction of the present invention, in at least one suitable downstream stage and to suitably recycle such separated propene as portion of the propene feed, namely as recycled propene stream, to the inventive epoxidation reaction. Such suitable and preferred downstream stage and the preferred compositions of such recycled propene stream is described in detail hereinunder.

According to a preferred embodiment, the propene feed employed in the process of the present invention, preferably comprised of the fresh propene feed stream and the recycled propene feed stream, are free of potassium cations ($K^+$) and free of phosphorus (P) in the form of anions of at least one phosphorus oxyacid. The term "free of potassium cations ($K^+$)" as used in this context of the present invention refers to a propene feed containing potassium cations ($K^+$) in an amount of less than 1 wt.-ppm, preferably less than 0.1 wt.-ppm. The term "free of phosphorus (P) in the form of anions of at least one phosphorus oxyacid" as used in this context of the present invention refers to a propene feed containing phosphorus (P) in the form of anions of at least one phosphorus oxyacid in an amount of less than 1 wt.-ppm, preferably less than 0.1 wt.-ppm, based on the total weight of propene feed stream.

As far the volume ratio of the fresh propene stream relative to the recycled propene stream is concerned, no specific restrictions exist. Suitably volume ratios are in the range of from 0.5 to 20, preferably from 1 to 10, more preferably from 2 to 5.

Methanol Feed

Generally, the fresh methanol stream can be employed as pure methanol stream containing only minor amounts of impurities. Preferably, the methanol feed as described above is technical grade methanol which, besides methanol, usually only contains traces of water as an impurity in amounts of 0.5 wt.-% at most, preferably 0.2 wt.-% at most. The recycled methanol stream as described above usually contains at least 95 wt.-% of methanol, the main impurity being water. This recycled methanol stream can also contain small amounts of organic impurities like acetaldehyde, propionaldehyde, dimethoxymethane, 1,1-dimethoxyethane, 1,1-dimethoxypropane, acetone, 4-methyl-1,3-dioxolane, 2,4-dimethyl-1,3-dioxolane and methyl formate. The total amount of these components in the recycled methanol stream is usually at most 1 wt.-%, preferably at most 0.5 wt.-%.

According to a preferred embodiment, the methanol feed employed in the process of the present invention, preferably comprised of the fresh methanol feed stream and the recycled methanol feed stream, are free of potassium cations ($K^+$) and free of phosphorus (P) in the form of anions of at least one phosphorus oxyacid. The term "free of potassium cations ($K^+$)" as used in this context of the present invention refers to a methanol feed containing potassium cations ($K^+$) in an amount of less than 1 ppm, preferably less than 0.1 wt.-ppm. The term "free of phosphorus (P) in the form of anions of at least one phosphorus oxyacid" as used in this context of the present invention refers to a methanol feed containing phosphorus (P) in the form of anions of at least one phosphorus oxyacid in an amount of less than 1 wt.-ppm, preferably less than 0.1 wt.-ppm, based on the total weight of methanol feed stream.

As far the volume ratio of the recycled methanol stream relative to the fresh methanol stream is concerned, no specific restrictions exist. Suitably volume ratios are in the range of from 10 to 2000, preferably from 50 to 1000, more preferably from 100 to 500.

Hydrogen Peroxide Feed

As far as the hydrogen peroxide feed is concerned, no specific restrictions exist with the proviso that the reaction feed comprising propene, methanol and hydrogen peroxide which is introduced into the reactor contains potassium cations ($K^+$) in the amount according to the present invention, and further contains phosphorus (P) in the form of anions of at least one phosphorus oxyacid.

In particular, the hydrogen peroxide feed can be prepared according to every conceivable method. It is conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxymonosulfuric acid to hydrogen peroxide and sulfuric acid which is thus obtained back. The preparation of hydrogen peroxide from the elements is also conceivable. Depending on the specific preparation method, the hydrogen peroxide feed can be, for example, an aqueous or an aqueous/methanolic hydrogen peroxide feed. In case an aqueous hydrogen peroxide feed is employed, the content of the feed with respect to hydrogen peroxide is usually in the range of from 3 to 85 wt.-%, preferably from 25 to 75 wt.-%, more preferably from 30 to 50 wt.-%, such as from 30 to 40 wt.-% or from 35 to 45 wt.% of from 40 to 50 wt.-%. In case an aqueous/methanolic hydrogen peroxide feed is employed, the content of the feed with respect to hydrogen peroxide is usually in the range of from 3 to 85 wt.-%, preferably from 4 to 25 wt.-%, more preferably from 5 to 15 wt.-%, and the mass ratio of hydrogen peroxide relative to water is usually at least 0.4, preferably in the range of from 0.4 to 17, more preferably in the range of from 0.6 to 6. According to a preferred embodiment of the present invention, an aqueous hydrogen peroxide feed is employed.

Therefore, the present invention relates to above-described process, wherein the hydrogen peroxide feed is an aqueous or a methanolic or an aqueous/methanolic, preferably an aqueous hydrogen peroxide feed, containing hydrogen peroxide preferably in an amount of from 25 to 75 wt.-%, more preferably of from 30 to 50 wt.-%.

According to the present, it is preferred to employ a hydrogen peroxide feed which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, $5^{th}$ edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most unpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference.

Therefore, the present invention also relates to above-described process, wherein as hydrogen peroxide feed, a crude aqueous hydrogen peroxide solution is employed obtained by extracting the reaction mixture of an anthraquinone process with water, preferably essentially pure water, said crude aqueous hydrogen peroxide solution containing hydrogen peroxide preferably in an amount of from 25 to 75 wt.-%, more preferably of from 30 to 50 wt.-%.

Further, the present invention also relates to above-described process, wherein as hydrogen peroxide feed, a crude aqueous hydrogen peroxide solution is employed obtained by extracting the reaction mixture of an anthraquinone process with water, preferably essentially pure water, said crude aqueous hydrogen peroxide solution containing hydrogen peroxide preferably in an amount of from 25 to 75 wt.-%, more preferably of from 30 to 50 wt.-%, and wherein, after extraction with water, preferably essentially pure water, the crude aqueous hydrogen peroxide solution is not subjected to a distillation stage and, is subjected to a further extraction stage.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 wt.-ppm sodium cations, from 100 to 700 wt.-ppm phosphorus calculated as phosphate ($PO_4^{3-}$), and from 50 to 400 wt.-ppm nitrate anions, in each case calculated with respect to hydrogen peroxide contained in the crude aqueous hydrogen peroxide solution. Preferred ranges are, e.g., from 50 to 200 wt.-ppm or from 50 to 100 wt.-ppm of sodium cations, from 100 to 500 wt.-ppm or from 100 to 300 wt.-ppm of phosphorus, and 50 to 200 wt.-ppm or 50 to 100 wt.-ppm of nitrate. Generally, the molar ratio of sodium relative to phosphorus calculated as phosphate is from 0.75 to 1.25 and the molar ratio of phosphorus calculated as phosphate relative to nitrate is from 0.5 to 2.5. Further, it is conceivable that other stabilizing agents such as stannites like, for example, sodium stannite ($Na_2SnO_2$) and/or organic phosphonic acids, in particular organic diphosphonic acids like etidronic acid are used.

As described above, it was surprisingly found that those reaction feeds show unexpected and advantageous effects which contain potassium cations ($K^+$) in an amount of from 110 to 190 micromol, relative to 1 mol hydrogen peroxide contained in the reaction feed, and further contains phosphorus (P) in the form of anions of at least one phosphorus oxyacid. Still further preferred are reaction feeds which contain $K^+$ in an amount of from 120 to 175 micromol, preferably of from 130 to 160 micromol, relative to 1 mol hydrogen peroxide contained in the reaction feed.

As far as the molar ratio of $K^+$ relative to P in the reaction feed is concerned, no specific restrictions exist. However, it was additionally found that it is preferred that this molar ratio is in a certain range. Preferably, in the reaction feed, the molar ratio of $K^+$ relative to P is in the range of from 0.75 to 1.0, preferably of from 0.8 to 0.95.

In particular due to the fact that according to a preferred embodiment, a crude aqueous hydrogen peroxide solution, more preferably a crude washed aqueous hydrogen peroxide solution is used as hydrogen peroxide feed which is/was admixed with the methanol feed and the propene feed to give the reaction feed, the present invention also relates to above-described process wherein the reaction feed additionally contains sodium ions ($Na^+$).

Preferably, in the reaction feed, the molar ratio of $K^+$ relative to $Na^+$ is greater than or equal to 0.1, more preferably greater than or equal to 0.2, more preferably greater than or equal to 0.5, more preferably greater than or equal to 1.0. Preferably, in the reaction feed, the molar ratio of $K^+$ relative to $Na^+$ is less than or equal to 3.0, more preferably less than or equal to 2.5, more preferably greater than or equal to 2.2, more preferably greater than or equal to 2.0.

According to still more preferred embodiments of the present invention, in the reaction feed, the molar ratio of $K^+$ relative to $Na^+$ is in the range of from 1.0 to 3.0, preferably from 1.2 to 1.75, more preferably of from 1.3 to 1.6.

Accordingly, it is especially preferred that in the reaction feed, the molar ratio of $K^+$ plus $Na^+$ relative to P is in the range of from 1.43 to 1.53, preferably from 1.44 to 1.52, more preferably of from 1.45 to 1.51.

As discussed above, it is a preferred embodiment of the present invention that above-described crude aqueous hydrogen peroxide solution, more preferably a crude washed aqueous hydrogen peroxide solution is employed as hydrogen peroxide feed. Such crude aqueous hydrogen peroxide solutions, more preferably crude washed aqueous hydrogen peroxide solutions generally have a $K^+$ content of less than 110 micromol, more preferably less than 70 micromol, more preferably less than 30 micromol, in particular less than 5 micromol, relative to 1 mol hydrogen peroxide contained in the hydrogen peroxide feed.

Therefore, the present invention relates to above-described process wherein the hydrogen peroxide feed contains in an amount of less than 110 micromol, preferably less than 70 micromol, more preferably less than 30 micromol, in particular less than 5 micromol, relative to 1 mol hydrogen peroxide contained in the hydrogen peroxide feed.

Therefore, the present invention relates to above-described process wherein the hydrogen peroxide feed contains $K^+$ in an amount of less than 110 micromol, preferably less than 70 micromol, more preferably less than 30 micromol, in particular less than 5 micromol, relative to 1 mol hydrogen peroxide contained in the hydrogen peroxide, and further contains from 50 to 400 wt.-ppm sodium cations, from 100 to 700 wt.-ppm phosphorus calculated as phosphate ($PO_4^{3-}$), and from 50 to 400 wt.-ppm nitrate anions, in each case calculated with respect to hydrogen peroxide contained in the crude aqueous hydrogen peroxide solution.

In view of this preferred embodiment of the present invention according to which above-described crude hydrogen peroxide solution, preferably above-described crude washed aqueous hydrogen peroxide solution obtained in the anthrachinone process with subsequent extraction with water, preferably essentially pure water, is used as hydrogen peroxide feed, it was found that in particular in view of the $K^+$ content of the reaction feed to be achieved, it is necessary to suitably increase the $K^+$ content, due to the fact that such crude hydrogen peroxide solutions, preferably such crude washed aqueous hydrogen peroxide solutions generally have a too low $K^+$ content, namely a content which is generally less than 110 micromol, more preferably less than 70 micromol, more preferably less than 30 micromol, in particular less than 5 micromol, relative to 1 mol hydrogen peroxide contained hydrogen peroxide feed. Increasing the $K^+$ content is conceivable via increasing the $K^+$ content of the hydrogen peroxide feed or via increasing the $K^+$ content of the methanol feed or via increasing the $K^+$ content of the propene feed or via increasing the content of the hydrogen peroxide feed and the methanol feed or via increasing the $K^+$ content of the methanol feed and the propene feed or via increasing the $K^+$ content of the hydrogen peroxide feed and the propene feed or via increasing the $K^+$ content of the hydrogen peroxide feed and the methanol feed and the propene feed. According to a preferred embodiment, at least the $K^+$ content of the methanol feed is increased. According to an especially preferred embodiment, only the $K^+$ content of the methanol feed is increased. Even more preferably, only the $K^+$ content of the methanol feed is increased by increasing the $K^+$ content of the recycled methanol stream as described above.

$K^+$ Containing Stream

Increasing the $K^+$ content can be performed according to every conceivable method. Generally, it is preferred to add at least one solution containing at least one, at least partially dissolved potassium salt to at least one of said feeds, preferably to at least the methanol feed, in particular only to the recycled methanol feed stream. Irrespective of the feed whose $K^+$ content is increased, it is preferred to employ at least one aqueous solution containing $K^+$ and further containing at least one suitable anion. As suitable anions, anions of at least one phosphorus oxyacid are preferred.

Therefore, the present invention relates to above-described process, wherein at least one solution containing $K^+$ and P in the form of anions of at least one phosphorus oxyacid is added to the hydrogen peroxide feed or to the propene feed or to the methanol feed or a mixed feed of two or three thereof, in such an amount that the reaction feed contains $K^+$ and P in the form of anions of at least one phosphorus oxyacid, in particular $K^+$, $Na^+$, and P in the form of anions of at least one phosphorus oxyacid, in amounts as described hereinabove.

According to the present invention, it is especially preferred to employ such solutions containing $K^+$ and P in the form of anions of at least one phosphorus oxyacid in which to molar ratio of $K^+$ relative to P is in the range of from 1.8 to 2.2, preferably in the range of from 1.9 to 2.1. Most preferably, the at least one solution is a solution of dipotassium hydrogen phosphate ($K_2HPO_4$), more preferably an aqueous solution of dipotassium hydrogen phosphate or a methanolic solution of dipotassium hydrogen phosphate or an aqueous/methanolic solution of dipotassium hydrogen phosphate, more preferably an aqueous solution of dipotassium hydrogen phosphate.

As far as the concentrations of the solutions containing $K^+$, preferably of the solutions containing $K^+$ and P in the form of anions of at least one phosphorus oxyacid, more preferably the solutions containing dipotassium hydrogen phosphate solutions, more preferably the aqueous dipotassium hydrogen phosphate solutions, are concerned, no specific restrictions exist. For example, the concentration can be chosen according to the scale of the epoxidation process wherein, for example, in an industrial scale process, the concentration may be comparatively high or wherein, in a laboratory scale process, the concentration may be comparatively low. Using high concentrations may be an advantage in case, for example, comparatively low amounts of solvent shall be additionally introduced into the epoxidation process. Such high concentrations of, for example, dipotassium hydrogen phosphate are in the range of at least 40 wt.-%, more preferably of at least 45 wt.-%, more preferably of at least 50 wt.-%, calculated on the basis of the total weight of the solution. However, dilute solutions with concentrations down to 1 wt.-% are also equally suitable and especially in the case the solution is added to the methanol feed, concentrations in the range of from 1 to 15 wt.-% are preferred, with the range of from 1 to 10 wt.-% being more preferred and the range of from 1 to 5 wt.-% being even more preferred.

While it is preferred to add these solutions containing $K^+$, preferably $K^+$ and P in the form of anions of at least one phosphorus oxyacid, to the hydrogen peroxide feed to increase the $K^+$ content thereof, it is also conceivable to add a suitable solution in the course of the process which leads to the hydrogen peroxide feed, for example in the anthrachinone process and/or the subsequent extraction stage. If, for example, the aqueous crude hydrogen peroxide solution is subjected to a further extraction stage wherefrom an aqueous crude washed hydrogen peroxide solution is obtained, it is also conceivable to add a suitable solution containing $K^+$, preferably $K^+$ and P in the form of anions of at least one phosphorus oxyacid in the course of this further extraction stage.

Therefore, the present invention relates to a continuous process for the production of propylene oxide comprising reacting propene with hydrogen peroxide in methanolic solution in the presence of a titanium silicalite-1 catalyst to obtain propylene oxide, wherein a reaction feed comprising propene, methanol and hydrogen peroxide is introduced into a reactor, said reaction feed containing potassium cations ($K^+$) in an amount of from 110 to 190 micromol, relative to 1 mol hydrogen peroxide contained in the reaction feed, and further containing phosphorus (P) in the form of anions of at least one phosphorus oxyacid, wherein the reaction feed is obtained from a hydrogen peroxide feed, a methanol feed, and a propene feed;

wherein the hydrogen peroxide feed contains $K^+$ in an amount of less than 110 micromol, preferably less than 70 micromol, more preferably less than 30 micromol, in particular less than 5 micromol, relative to 1 mol hydrogen peroxide contained in the hydrogen peroxide feed, said hydrogen peroxide feed preferably being a crude hydrogen peroxide solution obtained in the anthrachinone process with subsequent extraction with water, preferably essentially pure water or a crude washed hydrogen peroxide solution obtained from subjecting the crude hydrogen peroxide solution to a further extraction stage;

wherein at least one solution containing $K^+$ and P in the form of anions of at least one phosphorus oxyacid is added to the hydrogen peroxide feed or to the propene feed or to the methanol feed or a mixed feed of two or three thereof, preferably to the methanol feed, in such an amount that the reaction feed contains $K^+$ and P in the form of anions of at least one phosphorus oxyacid in amounts as defined in any of claims 1 to 7, said at least one solution containing $K^+$ and P in the form of anions of at least one phosphorus oxyacid preferably being an aqueous solution of dipotassium hydrogen phosphate.

Further, the present invention also relates the following embodiments, including the combinations of embodiments resulting from the respective back-references:

1. A process for the preparation of hydrogen peroxide, comprising
   preparing a reaction mixture via an anthrachinone process, wherein the anthrachinone compound preferably contains an alkyl residue having from 2 to 10, more preferably at least 5 carbon, more preferably 5 or 6 carbon atoms;
   preparing a crude hydrogen peroxide solution by subjecting the reaction mixture to an extraction stage using water, preferably essentially pure water as extracting agent, said crude hydrogen peroxide solution having a $K^+$ content of less than 110 micromol, preferably less than 70 micromol, more preferably less than 30 micromol, more preferably less than 5 micromol, relative to 1 mol hydrogen peroxide contained in the hydrogen peroxide solution;
   optionally subjecting the crude hydrogen peroxide solution to a further extraction stage to obtain a crude washed hydrogen peroxide solution;
   adding a solution containing $K^+$, preferably containing $K^+$ and P in the form of anions of at least one phosphorus oxyacid in which the molar ratio of $K^+$ relative to P is preferably in the range of from 1.8 to 2.2, more preferably in the range of from 1.9 to 2.1, to the crude hydrogen peroxide solution or to the crude washed hydrogen peroxide solution.
2. The process of embodiment 1, wherein the solution containing $K^+$, preferably containing $K^+$ and P in the form of anions of at least one phosphorus oxyacid, is added in an amount so that the $K^+$ content of the resulting hydrogen peroxide solution is in the range of from 110 to 190 micromol, preferably from 120 to 175 micromol, more preferably of from 130 to 160 micromol, relative to 1 mol hydrogen peroxide contained in the hydrogen peroxide solution.
3. The process of embodiment 1 or 2, wherein the solution containing $K^+$ and P in the form of anions of at least one phosphorus oxyacid is an aqueous dipotassium hydrogen phosphate ($K_2HPO_4$) solution.

As far as the content of the reaction feed with respect to other metal ions, alkali metal ions other than sodium and potassium, and/or alkaline earth metal ions is concerned, it is preferred in the context of the present invention that the total amount of (a) alkali metal ions other than $K^+$ and $Na^+$, (b) alkaline earth metal ions, and (c) other metal ions contained in the reaction feed is 5 micromol at most, preferably of 3 micromol at most, more preferably of 1 micromol at most, relative to 1 mol hydrogen peroxide contained the reaction feed.

As alkali metal ions other than $K^+$ and $Na^+$, $Li^+$, $Rb^+$, or $Cs^+$ may be mentioned by way of example. As earth alkaline metal ions, $Mg^{2+}$, $Ca^{2+}$, $Sr^{2+}$, $Ba^{2+}$ may be mentioned by way of example. As other metal ions, iron, aluminum, tin, palladium, chromium, nickel, manganese, molybdenum, vanadium and cobalt may be mentioned by way of example.

As discussed above, it is preferred to add above-discussed solutions containing $K^+$, preferably $K^+$ and P in the form of anions of at least one phosphorus oxyacid, to obtain a reaction feed containing $K^+$ in a concentration of 110 to 190 micromol. The amount of $K^+$ can be easily adjusted by the skilled person by suitably determining the amount of potassium. In the context of the present invention, the content of metals is to be understood as being determined by ICP-OES, optical emission spectroscopy after excitation in inductively coupled argon plasma. The amount of P is to be understood as being determined by ICP-OES.

Epoxidation Reaction

As described hereinabove, it is preferred to suitably mix the individual streams, namely the methanol feed stream, the hydrogen peroxide feed stream, and the propene feed stream, to obtain the reaction feed which comprises a liquid phase. Preferably, the individual streams are suitably mixed to obtain the reaction feed which consists of liquid phases. Even more preferably, the individual streams are suitably mixed to obtain the reaction feed which consists of one liquid phase. Therefore, the present invention is directed to above-described process wherein the reaction feed when introduced into the reactor consists of one liquid phase.

In the reaction feed, the molar ratio of propene relative to hydrogen peroxide is usually in the range of from 0.9 to 2.5, preferably from 1.0 to 2.0, more preferably from 1.05 to 1.5.

According to the present invention, this reaction feed is preferably introduced in a reactor where the epoxidation reaction is carried out in the presence of the titanium silicalite-1 catalyst. While it is generally conceivable to use the catalyst as suspension catalyst, it is preferred to employ the catalyst as fixed-bed catalyst. More preferably, the titanium silicalite-1 catalyst contains titanium silicalite-1 as catalytically active material embedded in a porous matrix, preferably in a mesoporous matrix, more preferably in a mesoporous silica matrix. A catalyst preferably employed according to the present invention is described in detail hereinunder. As to further reaction conditions under which the epoxidation reaction is carried, no specific restrictions exist.

Preferably, the pressure under which the reaction of propene with hydrogen peroxide in methanolic solution in the presence of the titanium silicalite-1 catalyst is carried out in the reactor is suitably chosen so that in the reactor, no gaseous phase is present. More preferably, the pressure under which the reaction of propene with hydrogen peroxide in methanolic solution in the presence of the titanium silicalite-1 catalyst is carried out in the reactor is at least 10 bar, preferably at least 15 bar, more preferably at least 20 bar and in particular in the range of from 20 to 40 bar. Generally, the reaction mixture in the reactor is suitably cooled. Preferably, the reaction mixture in the reactor is externally and/or internally cooled such that the maximum temperature of the reaction mixture in the reactor is in the range of from 30 to 70° C.

Generally, the epoxidation reaction according to the present invention can be carried out in at least one reactor. If more than one reactor is used, two or more reactors can be operated in series and/or two or more reactors can be operated in parallel. If two or more reactors are operated in series, the reaction mixture taken from a given reactor can be subjected to at least one intermediate treatment before it is fed to the next reactor. In such intermediate treatment, the physical and/or the chemical properties of the stream can be changed. For example, the temperature and/or the pressure of the stream can be changed, and/or the chemical composition of the stream can be changed, for example by reaction, distillation, and the like.

Preferably, the epoxidation reaction according to the present invention is carried out by a method comprising
(i) reacting propene with hydrogen peroxide in methanolic solution in the presence of the titanium silicalite-1 catalyst in at least one reactor R1, wherein a reaction feed comprising propene, methanol and hydrogen peroxide is introduced into R1, said reaction feed containing potassium cations ($K^+$) in an amount of from 110 to 190 micromol, relative to 1 mol hydrogen peroxide contained the reaction feed, and further containing phosphorus (P) in the form of anions of at least one phosphorus oxyacid;

(ii) separating a stream containing non-reacted hydrogen peroxide from the reaction mixture obtained from (i) and removed from R1;

(iii) mixing the stream containing non-reacted hydrogen peroxide with a propene stream, passing the mixed stream into at least 1 reactor R2 containing the titanium silicalite-1 catalyst and reacting propene with hydrogen peroxide in R2.

According to a preferred embodiment, the epoxidation process of the present invention consists of these three stages. According to an even more preferred embodiment, both reaction stages (i) and (iii) are carried out in continuous mode. The epoxidation reactions in stages (i) and (iii) are preferably carried out in fixed-bed mode.

In the inventive process, it is possible to use the same or different types of reactors in stages (i) and (iii). Thus, it is possible to carry out one of the reactions stages in an isothermal or adiabatic reactor and the other reaction stage, independently thereof, in an isothermal or adiabatic reactor. The term "reactor" as used in this respect comprises, as described above, a single reactor, a cascade of at least two serially connected reactors, at least two reactors which are operated in parallel, or a multitude of reactors wherein at least two reactors are serially coupled and wherein at least two reactors are operated in parallel. According to a preferred embodiment, stage (i) of the present invention is carried out in at least two reactors R1 which are operated in parallel, and stage (iii) of the present invention is carried out in a single reactor R2.

Each of the reactors described above, especially the reactors according to the preferred embodiment, can be operated in downflow or in upflow operation mode.

In case the reactors are operated in downflow mode, it is preferred to use fixed-bed reactors which are tubular, multitubular or multi-plate reactors, preferably equipped with at least one cooling jacket. In this case, the epoxidation reaction is carried out at a temperature of from 30 to 80° C., and the temperature profile in the reactors is maintained at a level so that the temperature of the cooling medium in the cooling jackets is at least 40° C. and the maximum temperature in the catalyst bed is 60° C. In the case of downflow operation of the reactors, it is possible to choose the reaction conditions such as temperature, pressure, feed rate and relative amounts of starting materials such that the reaction is carried out in a single phase, more preferably in a single liquid phase, or in a multiphase system comprising, for example, 2 or 3 phases. As to the downflow operation mode, it is especially preferred to conduct the epoxidation reaction in a multiphase reaction mixture comprising a liquid aqueous hydrogen peroxide rich phase containing methanol and a liquid organic olefin rich phase, preferably a propene rich phase.

In case the reactors are operated in upflow mode, it is preferred to use at least two fixed-bed reactors R1 in stage (i) and at least one reactor R2, preferably exactly one reactor R2 in stage (iii). According to a still further embodiment, the at least two reactors R1 used in stage (i) are serially connected or operated in parallel, more preferably operated in parallel. Generally, it is necessary to equip at least one of the reactors used in stage (i) and/or (iii) with a cooling means such as a cooling jacket. Especially preferably, the at least two reactors R1 which are employed in stage (i) are connected in parallel and can be operated alternately. In case the reactors are operated in upflow mode, the two or more reactors R1 connected in parallel in stage (i) are particularly preferably tube reactors, multi-tube reactors or multi-plate reactors, more preferably multi-tube reactors and especially preferably shell-and-tube reactors comprising a multitude of tubes such as from 1 to 20 000, preferably from 10 to 10 000, more preferably from 100 to 8000, more preferably from 1000 to 7000 and particularly preferably from 3000 to 6000 tubes. To regenerate the titanium silicalite-1 catalyst used for the epoxidation reaction, it is possible for at least one of the reactors connected in parallel in stage (i) to be taken out of operation for the respective reaction stage and the catalyst present in this reactor to be regenerated, with at least one reactor R1 always being available for reaction of the starting material or starting materials in every stage during the course of the continuous process.

As cooling medium used for cooling the reaction mixture in above-mentioned reactors equipped with cooling jackets, there are no specific restrictions. Especially preferred are oils, alcohols, liquid salts or water, such as river water, brackish water and/or sea water, which can in each case, for example, preferably be taken from a river and/or lake and/or sea close to the chemical plant in which the reactor of the invention and the process of the invention are used and, after any necessary suitable removal of suspended material by filtration and/or sedimentation, be used directly without further treatment for cooling the reactors. Secondary cooling water which is preferably conveyed around a closed circuit is particularly useful for cooling purposes. This secondary cooling water is generally essentially deionized or demineralised water to which at least one antifouling agent has preferably been added. More preferably, this secondary cooling water circulates between the reactor and, for example, a cooling tower. Preference is likewise given to the secondary cooling water being, for example, countercooled in at least one countercurrent heat exchanger by, for example, river water, brackish water and/or sea water.

In stage (iii), particular preference is given to using a continuously operated shaft reactor, and particularly preferably a continuously operated, adiabatic shaft reactor.

Therefore, the present invention also relates to a process as described above wherein in stage (i), at least two shell-and-tube reactors R1 each having of from 1 to 20,000 internal tubes and being continuously operated in upflow mode, said reactors R1 being operated in parallel, are employed, and wherein in stage (iii), an adiabatic shaft reactor R2 being continuously operated in upflow mode, is employed. Still more preferably, the reaction in at least one of these reactors, more preferably in the at least two reactors R1 of stage (i) and still more preferably in all reactors R1 and R2 used in stages (iii) and (c) is conducted such that in the respective reactor, no gaseous phase and preferably one single liquid phase is present.

The pressure in the reactors R1 and R2 used is generally at least 10 bar, preferably at least 15 bar, more preferably at least 20 bar and in particular in the range of from 20 to 40 bar. The temperature of the cooling medium, preferably the cooling water used for cooling the reaction mixture in the reactor, or reactors, R1 is in the range of preferably from 20 to 70° C., more preferably from 25 to 65° C. and particularly preferably from 30 to 60° C. The maximum difference between the temperature of the cooling medium, prior to cooling, and the maximum temperature in the catalyst fixed-bed is preferably at most 25K, more preferably less than 25K, more preferably at most 12K, more preferably less than 12K.

According to the preferred embodiment of the invention according to which the reactor or the reactors R1 in stage (i)

are fixed-bed reactors, the product mixture obtained therefrom essentially consists of propylene oxide, unreacted propylene, methanol, water, and hydrogen peroxide.

According to a further preferred embodiment of the present invention, the hydrogen peroxide conversion in R1 is preferably in the range of from 85 to 95%, more preferably in the range of from 87 to 93% such as in the range of from 87 to 90% or from 88 to 91% or from 89 to 92% or from 90 to 93%.

According to a preferred embodiment, the product mixture obtained from stage (i) has a methanol content in the range of from 55 to 75 wt.-%, especially preferably of from 60 to 70 wt.-%, based on the total weight of the product mixture, a water content in the range of from 5 to 25 wt.-%, especially preferably of from 10 to 20 wt.-%, based on the total weight of the product mixture, a propylene oxide content in the range of from 5 to 20 wt.-%, especially preferably of from 8 to 15 wt.-%, based on the total weight of the product mixture, and a propylene content in the range of from 1 to 10 wt.-%, especially preferably of from 1 to 5 wt.-%, based on the total weight of the product mixture.

The temperature of the product mixture obtained from stage (i) is preferably in the range of from 30 to 70° C. Prior to being fed to the distillation column of (b), the product mixture is preferably temperature adjusted in at least one heat exchanger to a temperature in the range of from 50 to 80° C., more preferably of from 60 to 70° C.

According to stage (ii), non-reacted hydrogen peroxide contained in the reaction mixture obtained from stage (i) and removed from R1 is separated from the reaction mixture obtained from stage (i). This separation is preferably carried out by distillation using at least one, preferably exactly one distillation column K1. The reaction mixture obtained from the at least one reactor, preferably from the at least two reactors R1 used in stage (i), comprising propylene oxide, methanol, water and non-reacted hydrogen peroxide, and further comprising non-reacted propene, is introduced into the distillation column K1.

The distillation column K1 configured as conventional distillation column is preferably operated at a top pressure of from 1 to 10 bar, more preferably of from 1 to 5 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar. According to an especially preferred embodiment, the distillation column K1 has from 5 to 60, preferably from 10 to 50 and especially preferably from 15 to 40 theoretical stages. At the top of the distillation column K1 of stage (ii), a stream essentially consisting of propylene oxide, methanol and propene is preferably obtained, having a water content of not more than 0.5 wt.-%, preferably of not more than 0.4 wt.-% and still more preferably of not more than 0.3 wt.-%, and having a hydrogen peroxide content of not more than 100 ppm, preferably of not more than 20 ppm and still more preferably of not more than 10 ppm, in each case based on the total weight of the mixture obtained at the top of the column. At the bottom of the distillation column K1 of stage (ii), a stream essentially consisting of methanol, water and hydrogen peroxide is preferably obtained, having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

According to a preferred embodiment, the distillation column K1 used in stage (ii) is configured as dividing wall column having at least one side-offtake, preferably one side-offtake. Preferably, the dividing wall column preferably has from 20 to 60, more preferably from 30 to 50 theoretical stages. The upper combined region of the inflow and offtake part of the dividing wall column preferably has from 5 to 50%, more preferably from 15 to 30%, of the total number of theoretical stages in the column, the enrichment section of the inflow part preferably has from 5 to 50%, more preferably from 15 to 30%, the stripping section of the inflow part preferably has from 15 to 70%, more preferably from 20 to 60%, the stripping section of the offtake part preferably has from 5 to 50%, more preferably from 15 to 30%, the enrichment section of the offtake part preferably has from 15 to 70%, more preferably from 20 to 60%, and the lower combined region of the inflow and offtake part of the column preferably has from 5 to 50%, more preferably from 15 to 30%, in each case of the total number of theoretical stages in the column. It is likewise advantageous for the inlet via which the product mixture obtained from (a) is fed into the column and the side offtake via which the a part of the methanol, preferably of from 0 to 50%, more preferably of from 1 to 40%, still more preferably of from 5 to 30% and especially preferably of from 10 to 25% of the methanol, is taken off as intermediate boiler and, still more preferably, directly fed back to stage (i), to be arranged at different heights in the column relative to the position of the theoretical stages. The inlet is preferably located at a position which is from 1 to 25, more preferably from 5 to 15 theoretical stages above or below the side offtake.

The dividing wall column preferably used in the process of the present invention is preferably configured either as a packed column containing random packing or ordered packing or as a tray column. For example, it is possible to use sheet metal or mesh packing having a specific surface area of from 100 to 1000 $m^2/m^3$, preferably from about 250 to 750 $m^2/m^3$, as ordered packing. Such packing provides a high separation efficiency combined with a low pressure drop per theoretical stage. In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions. The differential pressure over the dividing wall column can be utilized as regulating parameter for the heating power.

The distillation in the dividing wall column K1 is advantageously carried out at a pressure at the top of from 1 to 10 bar, preferably from 1 to 5 bar, more preferably from 1 to 3 bar and still more preferably of from 1 to 2 bar such as 1, 1.1, 1.2, 1.3, 1.4, 1.5, 1.6, 1.7, 1.8, 1.9 or 2 bar. The distillation is preferably carried out in a temperature range from 65 to 100° C., more preferably from 70 to 85° C. The distillation temperature is measured at the bottom of the column. At the top of the distillation column K1 of stage (ii), configured as dividing wall column, a stream essentially consisting of propylene oxide, methanol and propene is obtained, having a water content of not more than 500 ppm, preferably of not more than 400 ppm, and still more preferably of not more than 300 ppm, and having a hydrogen peroxide content of not more than 50 ppm, preferably of not more than 20 ppm and still more preferably of not more than 10 ppm, in each case based on the total weight of the mixture obtained at the top of the column. Furthermore, the top stream obtained has a propene content of from 15 to 35 wt.-%, preferably of from 20 to 30 wt.-% and still more preferably of from 20 to 25 wt.-%, a propylene oxide content of from 50 to 80 wt.-%, preferably of from 55 to 75 wt.-% and especially preferably of from 60 to 70 wt.-%, and a methanol content of from 5 to 20 wt.-%, more preferably of from 7.5 to 17.5 wt.-% and especially preferably of from 10 to 15 wt.-%, in each case based on the total weight of the top stream. At the side-offtake of the dividing wall distillation column K1, a stream essentially consisting of methanol and water is obtained having a methanol content of at least 95 wt.-%, preferably at least 96 wt.-% and still more preferably at least 97 wt.-%, and having a water content of not more than 5 wt.-%, preferably of not more than 3.5 wt.-% and still more preferably of not more than 2 wt.-%, in each case based on the total weight of the mixture obtained at the side-offtake of the column. At the bottom of the dividing wall distillation column K1, a stream essentially consisting of methanol, water and unreacted hydrogen peroxide is obtained having a propene content of not more than 50 ppm, preferably of not more than 10 ppm and still more preferably of not more than 5 ppm, and having a propylene oxide content of not more than 50 ppm, preferably of not more than 20 ppm and still more preferably of not more than 10 ppm, in each case based on the total weight of the mixture obtained at the bottom of the column.

At least part of the stream taken from the side of the dividing wall column K1 can be recycled as solvent into stage (i) of the inventive process. Preferably, at least 90%, more preferably at least 95% of the stream taken from the side-offtake are recycled into stage (i). According to the present invention, heating up the product stream obtained from stage (i) is carried out using, at least partially, the bottoms stream of the distillation column K1 of stage (ii). Preferably, of from 50 to 100%, more preferably of from 80 to 100% and especially preferably of from 90 to 100% of the bottoms stream obtained from the distillation column K1 used in (ii) are used for heating up the product stream obtained from (a) from a temperature in the range of from 45 to 55° C. to a temperature in the range of from 65 to 70° C.

The bottoms stream taken from the distillation column K1, preferably the dividing wall distillation column K1, essentially consisting of methanol, water and non-reacted hydrogen peroxide, is then fed to the reactor R2 of stage (iii). Preferably, the bottoms stream is cooled prior to being introduced into the reactor via, for example, one-stage cooling or two-stage cooling, more preferably to a temperature of from 20 to 40° C., still more preferably to a temperature of from 30 to 40° C. Still more preferably, fresh propene, is additionally added directly into the reactor R2 of stage (iii) or added to the bottoms stream obtained from K1 of stage (ii) prior to introducing same into the reactor R2 of stage (iii).

The selectivity of the overall process with stages (i) to (iii) with respect to hydrogen peroxide is preferably in the range from 78 to 99%, more preferably in the range from 88 to 97% and particularly preferably in the range from 90 to 96%. The total hydrogen peroxide conversion is preferably at least 99.5%, more preferably at least 99.6%, more preferably at least 99.7% and particularly preferably at least 99.8%.

The reaction mixture obtained from stage (iii) preferably has a methanol content of from 50 to 90 wt.-%, more preferably of from 60 to 85 wt.-% and especially preferably of from 70 to 80 wt.-%, based on the total weight of the reaction mixture. The water content is preferably in the range of from 5 to 45 wt.-%, more preferably of from 10 to 35 wt.-% and especially preferably of from 15 to 25 wt.-%, based on the total weight of the reaction mixture. The propylene oxide content is preferably in the range of from 1 to 5 wt.-%, more preferably of from 1 to 4 wt.-% and especially preferably of from 1 to 3 wt.-%, based on the total weight of the reaction mixture. The propylene content is preferably in the range of from 0 to 5 wt.-%, more preferably of from 0 to 3 wt.-% and especially preferably of from 0 to 1 wt.-%, based on the total weight of the reaction mixture.

As already mentioned above, it was found that the by-product selectivities are extremely low in case the reaction feed has the composition according to the invention. In particular, the total selectivity with regard to the sum of 1-methoxy-2-propanol, 2-methoxy-1-propanol, propylene glycol and oxygen is preferably at most 8.5%, more preferably at most 8.0%, based on hydrogen peroxide.

Therefore, the present invention also relates to above-described process, wherein the reaction of propene with hydrogen peroxide in methanolic solution in the presence of the titanium silicalite-1 catalyst is carried out by a method comprising (i) reacting propene with hydrogen peroxide in methanolic solution in the presence of the titanium silicalite-1 catalyst in at least one reactor R1 which is preferably operated in isothermal mode, wherein a reaction feed comprising propene, methanol and hydrogen peroxide is introduced into R1, said reaction feed containing potassium cations ($K^+$) in an amount of from 110 to 190 micromol, relative to 1 mol hydrogen peroxide contained in the reaction feed, and further containing phosphorus (P) in the form of anions of at least one phosphorus oxyacid;

(ii) separating a stream containing non-reacted hydrogen peroxide from the reaction mixture obtained from (i) and removed from R1, said separating preferably being carried out by distillation in at least 1, preferably 1 distillation column K1, more preferably 1 dividing wall distillation column K1;

(iii) mixing the stream containing non-reacted hydrogen peroxide with a propene stream, passing the mixed stream into at least 1, preferably 1 reactor R2, more preferably 1 shaft reactor R2, containing the titanium silicalite-1 catalyst and preferably being operated in adiabatic mode, and reacting propene with hydrogen peroxide in R2, wherein the hydrogen peroxide conversion in R1 is preferably in the range of from 85 to 95%, more preferably in the range of from 87 to 93%, and wherein the total hydrogen peroxide conversion after R2 is preferably at least 99.5%, more preferably at least 99.6%, more preferably at least 99.7% and particularly preferably at least 99.8%;

and wherein, according to a still further preferred embodiment, the total selectivity with regard to the sum of 1-methoxy-2-propanol, 2-methoxy-1-propanol, propylene glycol and oxygen is preferably at most 8.5%, more preferably at most 8.0%, based on hydrogen peroxide.

Titanium Silicalite-1 Catalyst

According to the present invention, a titanium silicalite-1 catalyst, preferably a fixed-bed titanium silicalite-1 catalyst, is employed as catalyst for the epoxidation of propene with hydrogen peroxide in methanol as solvent. Titanium silicalite-1 is a microporous zeolite of structure type MFI which contains no aluminum and in which the Si(IV) in the silicate lattice is partly replaced by titanium as Ti(IV). The term "micropores" as used in the context of the present invention relates to pores having a pore size smaller than 2 nm, determined according to DIN 66134.

The titanium silicalite-1 zeolite of the catalyst used in stages (i) and (iii) can in principle be prepared by any conceivable method. Typically, the synthesis of the at least one titanium zeolite according to the present invention is carried out in hydrothermal systems involving the combination of an active source of silicon oxide and a titanium source, such as titanium oxide, with at least one template compound capable of forming the desired titanium zeolite in an aqueous suspension, for example in a basic suspension. Typically, organic templates are employed. Preferably, the synthesis is carried out at elevated temperatures, for example temperatures in the range of from to 150 to 200° C., preferably from 160 to 180° C.

In principle, any suitable compound can be used as silicon oxide source. Typical sources of silicon oxide ($SiO_2$) include silicates, silica hydrogel, silicic acid, colloidal silica, fumed silica, tetraalkoxysilanes, silicon hydroxides, precipitated silica and clays. Both so-called "wet-process" silicon dioxide and so-called "dry-process" silicon dioxide can be employed. In these cases, the silicon dioxide is particularly preferably amorphous, wherein the size of the silicon dioxide particles is, for example, in the range of from 5 to 100 nm and the surface area of the silicon dioxide particles is, for example, in the range of from 50 to 500 $m^2/g$. Colloidal silicon dioxide is, inter alia, commercially available as Ludox®, Syton®, Nalco®, or Snowtex®. "Wet process" silicon dioxide is, inter alia, commercially available as Hi-Sil®, Ultrasil®, Vulcasil®, Santocel®, Valron-Estersil®, Tokusil® or Nipsil®. "Dry process" silicon dioxide is commercially available, inter alia, as Aerosil®, Reolosil®, Cab-O-Sil®, Fransil® or Arc-Silica®. It is as well within the scope of the present invention to use a silicon dioxide precursor compound as silicon oxide source. For example, tetraalkoxysilanes, such as for example, tetraethoxysilane or tetrapropoxysilane, may be mentioned as precursor compound.

As template, any template suitable to provide the desired MFI zeolitic structure can be used. In particular, tetrapropylammonium hydroxide, more preferably tetra-n-propylammonium hydroxide is employed. In a preferred embodiment of the process according to the invention, the at least one pore forming agent is removed in a later step by calcination, as described below.

Typically, the synthesis of the titanium silicalite-1 is carried out batchwise in an autoclave so that the reaction suspension is subjected to autogenous pressure for a number of hours or a few days until the titanium silicalite-1 zeolite is obtained. According to a preferred embodiment of the present invention, the synthesis generally proceeds at elevated temperatures wherein the temperatures during the hydrothermal crystallization step are typically in the range of from 150 to 200° C., preferably in the range of from 160 to 180° C. Usually, the reaction is carried out for a time in the range of a few hours to several days, preferably for a time in the range of from 12 h to 48 h, more preferably from 20 to 30 h. It is further conceivable to add seed crystals to the synthesis batches.

According to an embodiment of the present invention, the crystalline titanium silicalite-1 obtained is separated off from the reaction suspension, i.e. from the mother liquor, optionally washed and dried.

All methods known for the separation of the crystalline titanium silicalite-1 from the suspension can be employed. Inter alia, filtration, ultra-filtration, diafiltration and centrifugation methods should be mentioned.

In case the crystalline titanium silicalite-1 obtained is washed, said washing step can be carried out employing any suitable wash substance, such as, for example, water, alcohols, such as for example, methanol, ethanol, or methanol and propanol, or ethanol and propanol, or methanol and ethanol and propanol, or mixtures of water and at least one alcohol, such as, for example, water and ethanol or water and methanol, or water and ethanol, or eater and propanol, or water and methanol and ethanol, or water and methanol and propanol, or water and ethanol and propanol or water and ethanol and methanol and propanol. Water or a mixture of water and at least one alcohol, preferably water and ethanol, are used as wash substance.

Drying of the crystalline titanium silicalite-1 is effected at temperatures, in general, in the range of from 80 to 160° C., preferably from 90 to 145° C., particularly preferably from 100 to 130° C.

Instead of the above mentioned separation methods, such as, inter alia, filtration, ultra-filtration, diafiltration and centrifugation methods, the suspension may, according to an alternative embodiment, also be subjected to spray methods, as for example spray-granulation and spray-drying.

If the separation of the crystalline titanium silicalite-1 is carried out by means of spray method, the separating and drying step can be combined to a single step. In such case, either the reaction suspension as such or a concentrated reaction suspension can be employed. Additionally, it is possible to add a suitable additive as for example at least one suitable binder and/or at least one pore forming agent to the suspension—either to the reaction suspension as such or to the concentrated suspension—prior to spray drying or spray granulation. Suitable binders are described in detail below. As pore forming agent all pore forming agents described above can be used. In case the suspension is spray-dried, the pore forming agent—if added—may be added in two manners. First, the pore forming agent can be added to the reaction mixture prior to spray drying. However, it is also possible to add a portion of the pore forming agent to the reaction mixture prior to spray drying, with the remainder of the pore forming agent being added to the spray dried material.

In case the suspension is first concentrated to enhance the content of the titanium silicalite-1 in the suspension, concentration can be achieved, for example, by evaporating, as for example evaporating under reduced pressure, or by cross flow filtration. Like-wise, the suspension can be concentrated by separating said suspension into two fractions, wherein the solid contained in one of both fractions is separated off by filtration, diafiltration, ultrafiltration or centrifugation methods and is suspended after an optional washing step and/or drying step in the other fraction of the suspension. The thus obtained concentrated suspension can then be subjected to spray methods, as for example spray granulation and spray drying.

According to an alternative embodiment, concentration is achieved by separating the at least one titanium zeolite from the suspension, and re-suspending the titanium zeolite, optionally together with at least one suitable additive as already described above, wherein the titanium zeolite may be subjected to at least one washing step and/or at least one drying step prior to re-suspension. The re-suspended titanium zeolite can then be employed to spraying methods, preferably to spray drying.

Spray-drying is a direct method of drying slurries, suspensions or solutions by feeding a well-dispersed liquid-solid slurry, suspension or solution, often additionally containing a binder, to an atomizer and subsequently flash-drying in a stream of hot air. The atomizer can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single fluid nozzles which rely on hydrostatic pressure to force the slurry through a small nozzle. Multi-fluid nozzles are also used, where gas pressure is used to force the slurry through the nozzle. The sprayed material obtained using spray drying and spray granulation methods, like for example fluidized-bed drying, can contain solid and/or hollow spheres and can substantially consist of such spheres, which have, for example, a diameter in the range of from 5 to 500 µm or 5 to 300 µm. Single component or multiple component nozzles can be used. The use of a rotating sprayer is also conceivable. Possible inlet temperatures for the used carrier gas are, for example, in the range of from 200 to 600° C., preferably in the range of from 300 to 500° C. The outlet temperature of the carrier gas is, for example, in the range of from 50 to 200° C. Air, lean air or oxygen-nitrogen mixtures with an oxygen content of up to 10 vol.-%, preferably of up to 5 vol. %, more preferably of less than 5 vol. %, as, for example, of up to 2 vol. %, may be mentioned as carrier gases. The spray methods can be carried out in counter-current or co-current flow.

Preferably, the titanium silicalite-1 is separated from the reaction suspension by conventional filtration or centrifugation, optionally dried and/or calcined, and re-suspended, preferably in a mixture, preferably an aqueous mixture of at least one binder material and/or one pore-forming agent. The resulting suspension is then preferably subjected to spray-drying or spray-granulation. The obtained sprayed material may be subjected to an additional washing step, said washing step being carried out as described above. The optionally washed sprayed material is then dried and calcined wherein drying and calcination is preferably carried out as described above.

According to an alternative embodiment, the crystallization of the titanium silicalite-1 is effected not before the above described suspension has been spray dried. Therefore, first a suspension is formed comprising the source of silicon oxide, preferably silicon dioxide, the source of titanium oxide, and the template compound capable of forming the titanium silicalite-1. Then, the suspension is spray-dried, wherein subsequently, optionally additional pore forming agent is added to the spray-dried titanium silicalite-1.

The spray-dried titanium silicalite-1 obtained according to the above mentioned processes can, optionally, be subjected to at least one wash process If at least one wash process is carried out, preferably at least one drying step and/or at least one calcination step follows.

The titanium silicalite-1, optionally obtained by spraying methods, can further be subjected to at least one calcination step, which is carried out according to a preferred embodiment of the invention subsequent to the drying step, or instead of the drying step. The at least one calcination step is carried out at temperatures in general in the range of from 350-750° C., preferably form 400-700° C., particularly preferably from 450-650° C.

The calcination of the titanium silicalite-1 can be effected under any suitable gas atmosphere, wherein air and/or lean air is preferred. Furthermore, the calcinations is preferably carried out in a muffle furnace, rotary cone and/or a belt calcination furnace, wherein the calcination is generally carried out for one hour or more, for example for a time in the range of from 1 to 24 or from 4 to 12 hours. It is possible in the process according to the present invention, for example, to calcine the titanium silicalite-1 once, twice or more often for in each case at least one hour, for example in each case from 4 h to 12 h, preferably from 4 h to 8 h, wherein it is possible to keep the temperatures during the calcination step constant or to change the temperatures continuously or discontinuously. If calcination is effected twice or more often, the calcination temperatures in the individual steps may be different or identical.

Thus, a preferred embodiment of the present invention relates to a process as described above, wherein the titanium silicalite-1 separated off from the suspension, for example by filtration or spray drying, is washed with a suitable wash substance, and subsequently subjected to at least one drying step. Drying is effected at temperatures, in general, in the range of from 80 to 160° C., preferably from 90 to 145° C., particularly preferably from 100 to 130° C. Most preferably, after drying, a calcinations step is performed. The step is carried out at temperatures in general in the range of from 350-750° C., preferably form 400-700° C., particularly preferably from 450-650° C.

The titanium silicalite-1, prepared as described above, generally can be directly employed as catalyst in stages (i) and (iii). However, it is especially preferred to use a fixed-bed catalyst in both stages (i) and (iii), i.e. to employ not the crystalline zeolitic material per se as catalyst but the crystalline material processed to give a molding comprising the titanium silicalite-1. Thus, according to a preferred embodiment, a molding comprising the titanium silicalite-1, as described above, is employed as catalyst.

In general, in case a molding is employed as catalyst, said catalyst may comprise all conceivable further compounds in addition to the titanium silicalite-1 according to the invention, for example, inter alia, at least one binder and/or at least one pore forming agent. Furthermore, the catalyst may comprise at least one pasting agent instead of the at least one binder and/or the at least one pore forming agent or in addition to the at least one binder and/or the at least one pore forming agent.

As binder all compounds are suitable, which provide adhesion and/or cohesion between the titanium silicalite-1 to be shaped which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these compounds. Clay minerals and naturally occurring or synthetically produced aluminas, such as, for example, alpha-, beta-, gamma-, delta-, eta-, kappa-, chi- or theta-alumina and their inorganic or organometallic precursor compounds, such as, for example, gibbsite, bayerite, boehmite or pseudoboehmite or trialkoxyaluminates, such as, for example, aluminum triisopropylate, are particularly preferred as $Al_2O_3$ binders. Further preferred binders are amphiphilic compounds having a polar and a nonpolar moiety and graphite. Further binders are, for example, clays, such as, for example, montmorillonites, kaolins, metakaoline, hectorite, bentonites, halloysites, dickites, nacrites or anaxites.

These binders can be used as such. It is also within the scope of the present invention to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention binders which either completely or partly comprise $SiO_2$, or which are a precursor of $SiO_2$, from which $SiO_2$ is formed in at least one further step, are very particularly preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 m²/g.

Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Accordingly, the present invention also describes a catalyst containing a molding, as described above, said molding comprising the titanium silicalite-1 as described above and additionally $SiO_2$ as binder material wherein the binder used according to (I) is a binder comprising or forming $SiO_2$. Generally, the titanium zeolite can also be shaped without using a binder. Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder.

If desired, at least on pore forming agent can be added to the mixture of titanium silicalite-1 and at least one binder or at least binder-precursor, for further processing and for the formation of the catalyst shaped body to be employed as fixed-bed catalyst. Pore forming agents which may be used are all compounds which, with regard to the molding produced, provide a specific pore size and/or a specific pore size distribution and/or certain pore volumes. In particular, pore forming agents which provide, with regard to the molding produced, micropores and/or micropores, in particular mesopores and micropores.

Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder, the molding in particular having micropores and mesopores.

As regards examples for pore forming agents which may be used, reference is made to the pore forming agents already mentioned above. Preferably, the pore forming agents used in the shaping process of the invention are polymers which are dispersible, suspendable or emulsifiable in water or in aqueous solvent mixtures. Especially preferred polymers are polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents are, for example, pulp or graphite.

If desired for the pore size distribution to be achieved, a mixture of two or more pore forming agents may be used. In a particularly preferred embodiment of the process according to the invention, as described below, the pore forming agents are removed by calcination to give the porous catalyst shaped body. Preferably, pore forming agents which provide mesopores and/or micropores, particularly preferably mesopores, are added to the mixture of at least one binder and titanium silicalite-1 for shaping the titanium silicalite-1. Generally, the titanium silicalite-1 can also be shaped to obtain a catalyst shaped body without using a pore forming agent.

Besides binder and optionally pore forming agent it is as well possible to add additional components, for example at least one pasting agent, to the mixture which is shaped to obtain the catalyst shaped body.

If at least one pasting agent is used in the process of the invention, said pasting agent is used either instead of or in addition to the at least one pore forming agent. In particular, compounds which also act as pore forming agents can be used as pasting agent. Pasting agents which may be used are all compounds known to be suitable for this purpose. These are preferably organic, in particular hydrophilic polymers, such as, for example, cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, cellulose, cellulose derivatives, water and mixtures of two or more of these compounds, such as water and cellulose or water and cellulose derivatives are used as pasting agent. In a particularly preferred embodiment of the process according to the invention, the at least one pasting agents is removed by calcination, as further described below, to give the molding.

According to a further embodiment of the present invention, at least one acidic additive can be added to the mixture which is shaped to obtain the molding. If an acidic additive is used, organic acidic compounds which can be removed by calcination, are preferred. In this context carboxylic acids, such as, for example, formic acid, oxalic acid and/or citric acid, may be mentioned. It is also possible to use two or more of these acidic compounds.

The order of addition of the components to the mixture which is shaped to obtain the molding is not critical. If for example, a combination of a binder, a pore forming agent, a pasting agent and optionally at least one acidic compound is employed, it is possible both first to add the at least one binder then the at least one pore forming agent, the at least one acidic compound and finally the at least one pasting agent and to interchange the sequence with regard to the at least one binder, the at least one pore forming agent, the at least one acidic compound and the at least one pasting agent.

After the addition of at least one binder and/or at least one pasting agent and/or at least one pore forming agent and/or at least one acidic additive to the mixture comprising the titanium silicalite-1, the mixture is typically homogenized for 10 to 180 minutes. Inter alia, kneaders, edge mills or extruders are particularly preferably used for the homogenization. The mixture is preferably kneaded. On an industrial scale, grinding in an edge mill is preferred for the homogenization. The homogenization is, as a rule, carried out at temperatures in the range of from about 10° C. to the boiling point of the pasting agent and atmospheric pressure or slightly superatmospheric pressure. Optionally, at least one of the compounds described above can then be added. The mixture thus obtained is homogenized, preferably kneaded, until an extrudable plastic material is formed.

The homogenized mixture is then shaped to obtain a molding. All known suitable shaping methods, such as extrusion, spray drying, spray granulation, briquetting, i.e. mechanical compression with or without addition of additional binder or pelleting, i.e. compacting by circular and/or rotary movements, may be employed.

Preferred shaping methods are those in which conventional extruders are employed to shape the mixture comprising the titanium silicalite-1. Thus, for example extrudates having a diameter of from 1 to 10 mm and preferably of from 2 to 5 mm are obtained. In addition to the use of an extruder, an extrusion press can also be used for the preparation of the moldings. The shape of the moldings produced according to the invention can be chosen as desired. In particular, inter alia, spheres, oval shapes, cylinders or tablets are possible. Likewise, hollow structures, as for example hollow cylinders or honeycomb formed structures or also star-shaped geometries may be mentioned.

The shaping can take place at ambient pressure or at a pressure higher than ambient pressure, for example in a pressure range of from 1 bar to several hundred bar. Furthermore, the compacting can take place at ambient temperature or at a temperature higher than ambient temperature, for example in a temperature range of from 20 to 300° C. If drying and/or calcining are part of the shaping step, temperatures of up to 600° C. are conceivable. Finally, the compacting can take place in an ambient atmosphere or in a controlled atmosphere. Controlled atmospheres are, for example, inert gas atmospheres, reducing atmospheres and/or oxidizing atmospheres.

The shaping step is preferably followed by at least one drying step. This at least one drying step is carried out at temperatures in the range of in general from 80 to 160° C., preferably of from 90 to 145° C. and particularly preferably of from 100 to 130° C., usually for 6 h or more, for example in the range of from 6 to 24 h. However, depending on the moisture content of the material to be dried, shorter drying times, such as, for example, about 1, 2, 3, 4 or 5 h are also possible.

Before and/or after the drying step, the preferably obtained extrudate can, for example, be comminuted. Preferably granules or chips having a particle diameter of from 0.1 to 5 mm, in particular of from 0.5 to 2 mm, are obtained thereby.

According to a preferred embodiment of the present invention, the drying of the moldings, respectively, is preferably followed by at least one calcination step. Calcination is carried out at temperatures in general in the range of from 350-750° C., preferably form 400-700° C., particularly preferably from 450-650° C. The calcination can be effected under any suitable gas atmosphere, wherein air and/or lean air are preferred. Furthermore, the calcination is preferably carried out in a muffle furnace, a rotary kiln and/or a belt calcining furnace, wherein the duration of calcination is in general 1 h or more, for example in the range of from 1 to 24 h or in the range of from 3 to 12 h. In the process according to the invention, it is accordingly possible, for example, to calcine the catalyst shaped body once, twice or more often for in each case at least 1 h, such as, for example, in each case in the range of from 3 to 12 h, wherein it is possible for the temperatures during a calcination step to remain constant or to be changed continuously or discontinuously. If calcination is effected twice or more often, the calcination temperatures in the individual steps may be different or identical.

According to a particularly preferred embodiment, the catalyst shaped body is subjected to a hydrothermal treatment. Hydrothermal treatment can be carried out employing any suitable method known to those skilled in the art. Thus, the catalyst or catalyst shaped in general is contacted with water or water vapor. Typically, said hydrothermal treatment is carried out by charging the catalyst or according to the invention together with water into an autoclave, heating the slurry to a temperature in the range of from 100 to 200° C., preferably in the range of from 120 to 150° C. at a pressure in the range of from 1.5 to 5 bar, preferably in the range of from 2 to 3 bar, for a period in the range of from 1 to 48 hours, preferably in the range of from 24 to 48 hours. Typically at least one washing step, preferably with water as wash substance, follows. After the treatment with water the catalyst is being preferably dried and/or calcined, wherein drying and calcination is carried out as already described above. According to a preferred embodiment, the hydrothermal treatment is carried out by stirring the catalyst shaped body in an autoclave, wherein the stirring rate is adjusted to a stirring rate such that to avoid attrition as far as possible. If the catalyst is used in form of cylindrical extrudates, however, some attrition is desired to achieve cylindrical extrudates having rounded edges. With such extrudates having rounded edges, a higher bulk density can be achieved, for example for the use of the extrudates as fixed-bed catalyst in a tube reactor R1 and/or in a shaft reactor R2. Furthermore, the dust formation of said catalysts in the epoxidation process in stages (i) and (iii) is reduced.

Further, in the epoxidation process of the present invention, a titanium silicalite-1 catalyst as described above is employed, having micropores and mesopores, comprising from 49.5 to 80%, preferably 69.5 to 80% by weight of titanium silicalite-1, based on the total weight of the catalyst, and from 19.5 to 50%, preferably from 19.5 to 30% by weight of at least one binder, preferably a silica binder, based on the total weight of the catalyst shaped body.

Downstream Stages

The product mixture taken from the reactor R2 of stage (iii) can be fed to further down-stream stages where high-purity propylene oxide is suitably separated from said product mixture. Additionally, the stream taken from the top of the distillation column K1 of stage (ii) can be combined with the product mixture taken from the reactor R2 of stage (iii) which is then fed to said downstream purification stages. Alternatively, it is possible to separately feed the product mixture taken from the reactor R2 of stage (iii) and the top stream of the distillation column K1 of stage (ii) to said downstream purification stages. Preferably, the combined stream (M) consisting of the reaction mixture obtained from (iii) and removed from R2, and the top stream obtained from K1, are fed to said downstream purification stages. In the following, said stream (M) is also referred to as mixture (M).

Stage (iv)

According to a stage (iv), unreacted propene is preferably separated from the mixture (M) by distillation to obtain a mixture (M-iv1) comprising at least 80 wt.-% of propene and a mixture (M-iv2) comprising methanol, water and at least 7 wt.-% of propylene oxide.

Separation according to stage (iv) is preferably carried out in at least one distillation column K2, more preferably in one distillation column K2. Preferably, this column K2 has of from 5 to 40, more preferably of from 10 to 35 and especially preferably of from 15 to 30 theoretical stages. The distillation column K2 is preferably operated at a top pressure of from 1 to 5 bar, more preferably of from 1 to 4 bar, more preferably of from 1 to 3 bar and still more preferably of from 1 to 2 bar such as 1, 1.1, 1.2, 1.3, 1.4, 1.5, 1.6, 1.7, 1.8, 1.9 or 2 bar.

Preferably, mixture (M-iv1) is obtained at the top of the distillation column K2 comprising at least 85 wt.-% of propene, still more preferably of from 85 to 90 wt.-% of propene. As discussed above, in the context of the present invention, it is possible to introduce fresh propene as chemical grade propene into the inventive epoxidation reaction. In case such chemical grade propene is used, the mixture (M-iv1) can additionally comprise up to 15 wt.-%, preferably of from 5 to 10 wt.-% of propane, based on the total weight of mixture (M-iv1). The top stream obtained from distillation column K2 preferably has a propylene oxide content of 200 vol.-ppm at most, preferably of 150 vol.-ppm at most, more preferably of 100 vol.-ppm at most.

As discussed above, propene which has not reacted in the course of the epoxidation reaction is preferably separated in at least one downstream stage and recycled as recycled propene stream. More preferably, it is the mixture (M-iv1) which is recycled as recycled propene stream, optionally after having been subjected to at least one further purification stage. Such further purification stage may include, for example, a method comprising (aa) compressing and cooling the gaseous mixture (M-iv1);
(bb) separating propene from the resulting mixture by absorbing the propene in an absorbent;
(cc) separating the propene from the absorbent by desorption; wherein compressing or cooling or compressing and cooling in (aa) is carried out at least twice, compressing and cooling in (aa) more preferably being carried out three times.

Preferably, this method comprises (aa) compressing the gaseous mixture (M-iv1) at a pressure of from 13 to 18 bar and cooling the compressed mixture at a temperature of from 30 to 45° C. and repeating compressing and cooling once or twice, wherein from 50 to 90 percent by weight of the propene, from 60 to 99 percent by weight of the methanol and/or from 70 to 99.5 percent by weight of the water, comprised in the mixture (M-iv1), are condensed and preferably recirculated into the epoxidation reaction;
(bb) separating the propene from the compressed and cooled mixture by absorbing the propene at a pressure of from 13 to 18 bar in an absorbent, said absorbent having a boiling point of from 200 to 300° C. at standard pressure and being a mixture of hydrocarbons $C_nH_{2n+2}$ wherein n is from 13 to 15, said mixture comprising the hydrocarbon $C_{14}H_{30}$ in an amount of 30 percent by weight or more of the mixture;
(cc) separating the propene from the absorbent by desorption in a separation column at a pressure of from 16 to 25 bar and a temperature of from 50 to 200° C., and
recirculating the propene obtained in (cc) into said epoxidation reaction and recirculating the absorbent into (bb).

Preferably, after the desorption step (cc), the obtained mixture is preferably fed to at least one further purification stage. In this further purification stage, the mixture is preferably fractioned into the components propene and propane. Said fractionating is preferably carried out in a $C_3$ splitter as described, for example, in Ullmann's Encyclopedia of Industrial Chemistry, 5$^{th}$ Edition, Volume A22, page 214. The separation can be carried out in a column at a pressure of from about 15 to 25 bar. The separation can also be carried out using thermally coupled columns, and these are, for example, operated at a pressure of about 15 or 25 bar. The propene is taken off at the top of the $C_3$ splitter configured as a column, and the propane is taken off at the bottom This propene taken off at the top is preferably recycled as recycle propene stream to the epoxidation reaction.

Said method comprising steps (aa) to (cc) is described in detail in WO 2005/103024 A1 which is incorporated herein by reference. In particular, the example of WO 2005/103024 A1, on page 27, line 8 to page 28, line 22 is incorporated herein by reference, as well as embodiments 1 to 20 and their specific combinations, disclosed on page 24, line 28 to page 26, line 41.

According to another preferred embodiment, instead of steps (bb) and (cc), steps (bb') and (cc') are carried out comprising (bb') adding hydrogen to the compressed and cooled mixture and reducing the oxygen comprised in mixture (GII) at least partially by reaction with hydrogen in the presence of a catalyst comprising copper in elemental and/or oxide form on a support, wherein copper is present on the support in an amount of 30 to 80 wt.-%, preferably 40 to 50 wt.-%, based on the whole catalyst and calculated as CuO;
(cc') separating propene from the mixture resulting from (aa') and re-introducing the separated propene into the epoxidation reaction.

Said method comprising steps (aa), (bb') and (cc') is described in detail in WO 2010/130610 A1 which is incorporated herein by reference concerning the general and specific disclosure of steps (bb') and (cc'), in WO 2010/130610 A1 referred to as steps (III) and (IV). In particular, the examples of WO 2010/130610 A1, on page 48, ll. 19-22 (preparation of copper catalyst), on page 48, line 24 to page 49, line 24 (1$^{st}$ hydrogenation example), and on page 49, line 26 to page 50, line 16 (2$^{nd}$ hydrogenation example) are incorporated herein by reference.

Preferably, the mixture (M-iv2) obtained as bottoms stream comprises of from 55 to 80 wt.-%, more preferably from 60 to 75 wt.-% and especially preferably from 65 to 70 wt.-% of methanol, of from 13 to 25 wt.-%, more preferably from 15 to 20 wt.-% of water, and at least 7 wt.-%, more preferably at least 8 wt.-%, more preferably at least 9 wt.-% and especially preferably at least 10 wt.-%, for example from 10 to 15 wt.-% such as about 10, about 11, about 12, about 13, about 14 or about 15 wt.-% of propylene oxide. The bottoms stream obtained from distillation column K2 preferably has a propene content of 200 wt.-ppm at most, preferably of 150 wt.-ppm at most, more preferably of 100 wt.-ppm at most.

According to a preferred embodiment, distillation column K2 has an external reflux wherein at least one suitable solvent is added to the column. Most preferably, methanol is used as external reflux. Yet more preferably, at least a portion of mixture (M-v2) as described in detail in following section "Stage (v)" is used as external reflux.

Stage (v)

Preferably, according to a stage (v), mixture (M-iv2) obtained from stage (iv) as bottoms stream is subjected to a further distillative separation process in which a mixture (M-v1) comprising at least 98 wt.-% of propylene oxide and a mixture (M-v2) comprising water, at least 55 wt.-% of methanol and at most 100 wt.-ppm of propylene oxide are obtained.

Separation according to stage (v) is preferably carried out in at least one distillation column K3, more preferably in one distillation column K3. Preferably, this column K3 has of from 30 to 110, more preferably of from 40 to 100 and especially preferably of from 50 to 90 theoretical stages.

The distillation column K3 is preferably operated at a top pressure of from 1 bar or less. Especially preferably, the distillation column K3 is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

According to a preferred embodiment, the mixture (M-v1) obtained as top stream from K3 comprises at least 99 wt.-%, preferably at least 99.1 wt.-%, more preferably at least 99.2 wt.-%, more preferably at least 99.3 wt.-%, more preferably at least 99.4 wt.-%, and still more preferably at least 99.5 wt.-% of propylene oxide. Preferred contents of (M-v1) with respect to propylene oxide are, for example, in the range of from 99.1 to 99.9, more preferably from 99.2 to 99.9, more preferably from 99.3 to 99.9, more preferably from 99.4 to 99.9 and still more preferably from 99.5 to 99.9 wt.-%, based on the total weight of mixture (M-v1).

According to a preferred embodiment, the mixture (M-v2) obtained as bottoms stream from K3 comprises of from 55 to 85 wt.-%, more preferably from 65 to 80 wt.-% and especially preferably from 75 to 80 wt.-% of methanol, and of from 15 to 45 wt.-%, more preferably from 20 to 35 wt.-% and especially preferably of from 20 to 25 wt.-% of water, wherein the content of mixture (M-v2) regarding methanol as well as water is higher than the respective content of mixture (M-iv2). Further, the bottoms stream obtained from K3 preferably has a propylene oxide content of 200 wt.-ppm at most, more preferably of 150 wt.-ppm at most, more preferably of 100 wt.-ppm at most.

Preferably, said stream (M-v2) is fed as external reflux into the distillation column K2 used in stage (iv) as described above.

According to a further embodiment of the present invention, separation of propylene oxide in stage (v) is performed in at least two, more preferably in two distillation columns K3, namely K31 and K32.

Therefore, the present invention also relates to a process as described above, wherein in (v), the propylene oxide is separated in two distillation columns K31 and K32, wherein from the first distillation column K31, a mixture comprising at least 98 wt.-% of propylene oxide is obtained, said mixture being introduced into the second distillation column K32, from which a propylene oxide stream comprising at least 99.8 wt.-% propylene oxide is obtained. Still more preferably, the propylene oxide stream obtained from the second distillation column K32 comprises at least 99.9 wt.-% of propylene oxide, still more preferably at least 99.99 wt.-% of propylene.

Preferably, the first column K31 has of from 30 to 110, more preferably of from 40 to 100 and especially preferably of from 50 to 90 theoretical stages. The first column K3 is preferably operated at a top pressure of from 1 bar or less. Especially preferably, the distillation column K3 is operated as a vacuum column at a top pressure of less than 1 bar, more preferably at not more than 0.9 bar, more preferably at not more than 0.8 bar, more preferably at not more than 0.7 bar, and still more preferably at not more than 0.6 bar. Preferred ranges of the top pressure are, for example, from 0.3 to 0.9 bar, more preferably from 0.4 bar to 0.8 bar. Preferred top pressures are, for example, about 0.4 bar or about 0.5 bar or about 0.6 bar or about 0.7 bar or about 0.8 bar.

Preferably, the second column K32 has of from 25 to 60, more preferably of from 30 to 55 and especially preferably of from 35 to 50 theoretical stages. The second column K32 is preferably operated at a top pressure of from 1 to 7 bar, more preferably from 2 to 6 bar and especially preferably from 3 to 5 bar.

The mixture obtained from the top of the first column K31 which is fed as feed stream to the second column K32 can further contain certain by-products resulting from one or more stages of the overall epoxidation process. Examples for such by-products are aldehydes such as, for example, acetaldehyde and/or formaldehyde. These byproducts can be contained in the top stream of the first column K31 in an amount of up to 0.3 wt.-%, preferably up to 0.20 wt.-% and especially preferably up to 0.15 wt.-%, based on the total weight of (M-v2) and referring to the sum of the respective weights of these low-boiling compounds.

Therefore, the present invention relates to above-described process, further comprising (iv) distilling a combined stream consisting of the reaction mixture obtained from (iii) and removed from R2, and the top stream obtained from K1, in a distillation column K2 to obtain a top stream having a propylene oxide content of 100 vol.-ppm at most and a bottoms stream having a propene content of 100 wt.-ppm at most, said distilling preferably being carried out using a methanol stream as external reflux;

(v) distilling the bottoms stream obtained from (iv) in a distillation column K3 to obtain a top stream mixture containing at least 98 wt.-% of propylene oxide and a bottoms stream having a propylene oxide content of 100 wt.-ppm at most.

Further, the present invention relates to a mixture containing at least 98 wt.-% of propylene oxide, obtainable or obtained by above-described process, further comprising (iv) distilling a combined stream consisting of the reaction mixture obtained from (iii) and removed from R2, and the top stream obtained from K1, in a distillation column K2 to obtain a top stream having a propylene oxide content of 100 vol.-ppm at most and a bottoms stream having a propene content of 100 wt.-ppm at most, said distilling preferably being carried out using a methanol stream as external reflux;

(v) distilling the bottoms stream obtained from (iv) in a distillation column K3 to obtain a top stream mixture containing at least 98 wt.-% of propylene oxide and a bottoms stream having a propylene oxide content of 100 wt.-ppm at most.

Preferably, said mixture containing at least 98 wt.-% of propylene oxide which is obtainable or obtained by the process above in step (v) as top stream mixture has a very low content of by-products such as acetaldehyde, methyl formate, and water. Typically, said mixture contains at most 50 ppm, preferably at most 30 ppm, more preferably at most 25 ppm acetaldehyde, at most 100 ppm, preferably at most 80 ppm, more preferably at most 75 ppm methyl formate, and at most 50 ppm, preferably at most 40 ppm, more preferably at most 30 ppm water.

Therefore, the present invention also relates to a mixture containing at least 98 wt.-%, preferably at least 99 wt.-%, more preferably at least 99.9 wt.-%, more preferably at least 99.99 wt.-% of propylene oxide, obtainable or obtained by a process comprising, optionally consisting of (i) reacting propene with hydrogen peroxide in methanolic solution in the presence of the titanium silicalite-1 catalyst in at least one reactor R1 which is preferably operated in isothermal mode, wherein a reaction feed comprising propene, methanol and hydrogen peroxide is introduced into R1, said reaction feed containing potassium cations ($K^+$) in an amount of from 110 to 190 micromol, relative to 1 mol hydrogen peroxide contained in the reaction feed, and further containing phosphorus (P) in the form of anions of at least one phosphorus oxyacid;

(ii) separating a stream containing non-reacted hydrogen peroxide from the reaction mixture obtained from (i) and removed from R1, said separating preferably being carried out by distillation in at least 1, preferably 1 distillation column K1, more preferably 1 dividing wall distillation column K1;

(iii) mixing the stream containing non-reacted hydrogen peroxide with a propene stream, passing the mixed stream into at least 1, preferably 1 reactor R2, more preferably 1 shaft reactor R2, containing the titanium silicalite-1 catalyst and preferably being operated in adiabatic mode, and reacting propene with hydrogen peroxide in R2;

(iv) distilling a combined stream consisting of the reaction mixture obtained from (iii) and removed from R2, and the top stream obtained from K1, in a distillation column K2 to obtain a top stream having a propylene oxide content of 100 vol.-ppm at most and a bottoms stream having a propene content of 100 wt.-ppm at most, said distilling preferably being carried out using a methanol stream as external reflux;

(v) distilling the bottoms stream obtained from (iv) in a distillation column K3 to obtain a top stream mixture containing at least 98 wt.-% of propylene oxide and a bottoms stream having a propylene oxide content of 100 wt.-ppm at most.

said mixture being obtained as top stream mixture in (v).

Preferably, this top stream mixture contains at most 10 wt.-ppm, preferably at most 5 wt.-ppm, more preferably at most 2 wt.-ppm of formaldehyde; at most 10 wt.-ppm, preferably at most 7 wt.-ppm, more preferably at most 4 wt.-ppm, methylformate; at most 10 wt.-ppm, preferably at most 8 wt.-ppm, more preferably at most 6 wt.-ppm methanol; at most 75 wt.-ppm, preferably at most 70 wt.-ppm, more preferably at most 65 wt.-ppm water.

Therefore, the present invention also relates to a mixture containing at least 99.99 wt.-% propylene oxide, preferably obtainable or obtained by above-described process comprising stages (i) to (v), said mixture comprising at most 2 wt.-ppm of formaldehyde, at most 4 wt.-ppm, methylformate, at most 6 wt.-ppm methanol, and at most 65 wt.-ppm water.

According to a further preferred embodiment of the present invention, said mixture contains less than 5 wt.-ppm, preferably less than 4 wt.-ppm, more preferably less than 3 wt.-ppm acetaldehyde. In particular, the acetaldehyde content of the mixtures of the present invention is below the detection limit and thus, has to be considered to be free of acetaldehyde.

Therefore, the present invention also relates to a mixture containing at least 99.99 wt.-% propylene oxide, preferably obtainable or obtained by above-described process comprising stages (i) to (v), said mixture comprising less than 3 wt.-ppm acetaldehyde, preferably being free of acetaldehyde, and, more preferably, further comprising at most 2 wt.-ppm of formaldehyde, at most 4 wt.-ppm, methylformate, at most 6 wt.-ppm methanol, and at most 65 wt.-ppm water.

According to a further preferred embodiment of the present invention, said mixture contains less than 5 wt.-ppm, preferably less than 4 wt.-ppm, more preferably less than 3 wt.-ppm propene; less than 5 wt.-ppm, preferably less than 4 wt.-ppm, more preferably less than 3 wt.-ppm propane; less than 20 wt.-ppm, preferably less than 15 wt.-ppm, more preferably less than 10 wt.-ppm 1,1-dimethoxyethane; less than 10 wt.-ppm, preferably less than 7 wt.-ppm, more preferably less than 5 wt.-ppm dimethoxymethane; less than 20 wt.-ppm, preferably less than 15 wt.-ppm, more preferably less than 10 wt.-ppm 1,1-dimethoxypropane; less than 20 wt.-ppm, preferably less than 15 wt.-ppm, more preferably less than 10 wt.-ppm 4-methyl-1,3-dioxolane; and less than 10 wt.-ppm, preferably less than 7 wt.-ppm, more preferably less than 5 wt.-ppm propionaldehyde. In particular, each of these compounds is below the detection limit and thus, the mixture of the present invention has to be considered to be free of each of these compounds.

According to a further stage (vi), mixture (M-v2) obtained from stage (v) as bottoms stream is preferably subjected to a further distillative separation process. Optionally, after stage (v) and prior to stage (vi), a catalytic hydrogenation stage can be arranged. In such catalytic hydrogenation stage, the mixture (M-v2) obtained from stage (v) is preferably subjected to hydrogenation in the presence of a hydrogenation catalyst which comprises a catalytically active metal selected from the group consisting of Pd, Pt, Rh, Ir, Os and a mixture of two or more thereof. Preferably, such hydrogenation reaction can be carried out at a temperature of from 65 to 85° C. and at a hydrogen partial pressure of from 3 to 20 bar, preferably of from 3 to 13 bar. Details concerning preferred reaction conditions and preferred catalysts, and also the preparation, activation and regeneration of the preferred catalysts can be found in WO 2007/074101 A1 which, with respect to the catalytical hydrogenation and the catalysts used therefor, is incorporated herein by reference. If such hydrogenation stage is performed, the mixture obtained therefrom, referred to in the following as mixture (M-v2'), is subjected to stage (vi) of the present invention.

Stage (vi)

According to a stage (vi), mixture (M-v2) obtained from stage (v) as bottoms stream, or optionally (M-v2') obtained from the hydrogenation stage, is preferably subjected to a further distillative separation process in which a mixture (M-vi1) comprising at least 85 wt.-% of methanol and up to 10 wt.-% of water, and a mixture (M-vi2) comprising at least 90 wt.-% of water are obtained.

Distillation in stage (vi) can be performed in one, two, three or more distillation columns K4.

According to one embodiment, distillation in stage (vi) is carried out in one distillation column K4. Preferably, this distillation column K4 has of from 10 to 100, more preferably of from 20 to 90 and especially preferably of from 30 to 70 theoretical stages. The distillation column K4 is operated at a pressure preferably of from 1 to 12 bar, more preferably of from 2 to 11 bar and especially preferably of from 3 to 10 bar. The mixture (M-vi1) obtained from the top of the column K4 comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water, more preferably at least 97 wt.-% of methanol and up to 3 wt.-% of water, more preferably at least 98 wt.-% of methanol and up to 2 wt.-% of water, more preferably at least 98.5 wt.-% of methanol and up to 1.5 wt.-% of water, more preferably at least 98.5 wt.-% of methanol and up to 1 wt.-% of water. The reflux ratio of this column is preferably in the range of 1 to 10, more preferably in the range of 2 to 8.

According to a preferred embodiment, distillation in stage (vi) is performed in a two-pressure distillation process, where in a first distillation column K41, distillation is carried out at a top pressure which is different from the top pressure of the second distillation column K42. According to a still further preferred embodiment, the columns K41 and k42 are thermally coupled. According to one embodiment, the condenser used to condense the top stream of the first or second distillation column is used simultaneously as the vaporizer of the second or first distillation column. Preferably, the condenser used to condense the top stream obtained from the second distillation column is used simultaneously as the vaporizer of the first distillation column. According to still further embodiment, the bottoms stream obtained from column K41 which is fed as input stream into column K42 is heated, prior to being introduced into K42, with the bottoms stream obtained from column K42. According to a preferred embodiment, these thermal coupling possibilities are combined.

The distillation in the first column K41 is preferably carried out at a top pressure in the range of from 2 to 8 bar, more preferably of from 2 to 6 bar and especially preferably in the range of from 2.5 to 6 bar. The distillation in the second column (K2) is preferably carried out at a top pressure in the range from 8 to 15 bar, more preferably of from 8.5 to 14 bar, and especially preferably in the range from 9 to 13 bar. Distillation column K41 has preferably of from 5 to 30, more preferably from 7 to 25 and especially preferably of from 10 to 20 theoretical stages. Preferably, the bottoms stream obtained from K41 is heated to a temperature from 110 to 180° C., more preferably from 120 to 180° C., more preferably from 130 to 175° C. and still more preferably from 140 to 170° C.

The reflux ratio of column K42 is preferably in the range of from 1 to 5, more preferably of from 2 to 4. The reflux ratio is defined as the mass flow of the top stream obtained from column K42 divided by the mass flow of the fraction of this stream fed back to the top of K42. Distillation column K42 has preferably of from 5 to 60, more preferably from 10 to 55 and especially preferably of from 15 to 50 theoretical stages.

Preferably, distillation column K42 is configured as dividing wall column having at least one side-offtake, preferably one side-offtake. Preferably, the dividing wall column K42 has from 10 to 60, more preferably from 15 to 50 theoretical stages. The upper combined region of the inflow and offtake part of the dividing wall column preferably has from 10 to 70%, more preferably from 15 to 55%, the enrichment section of the inflow part preferably has from 5 to 50%, more preferably from 15 to 30%, the stripping section of the inflow part preferably has from 5 to 50%, more preferably from 15 to 30%, the stripping section of the offtake part preferably has from 5 to 50%, more preferably from 15 to 30%, the enrichment section of the offtake part preferably has from 5 to 50%, more preferably from 15 to 30%, and the lower combined region of the inflow and offtake part of the column preferably has from 5 to 50%, more preferably from 15 to 30%, in each case of the total number of theoretical stages in the column. The dividing wall column is preferably configured either as a packed column containing random packing or ordered packing or as a tray column. For example, it is possible to use sheet metal or mesh packing having a specific surface area of from 100 to 1000 m$^2$/m$^3$, preferably from about 250 to 750 m$^2$/m$^3$, as ordered packing. Such packing provides a high separation efficiency combined with a low pressure drop per theoretical stage. In the abovementioned configuration of the column, the region of the column divided by the dividing wall, which consists of the enrichment section of the inflow part, the stripping section of the offtake part, the stripping section of the inflow part and the enrichment section of the offtake part, or parts thereof is/are provided with ordered packing or random packing. The dividing wall can be thermally insulated in these regions.

Compared to a conventional distillation column, the dividing wall column used in stage (d) has the advantage that certain by-products resulting from one or more stages of the overall epoxidation process can be easily separated from methanol which is an advantage since mixture (M-vi1) is most preferably fed back as recycled methanol feed stream into stage (i) of the epoxidation process, as described above.

In case stage (vi) is performed as two-pressure distillation using a conventional distillation column K41 and a dividing wall column K42, the top stream obtained from the top of column K41 comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water and especially preferably at least 97 wt.-% of methanol and up to 3 wt.-% of water. According to particularly preferred embodiment, the top stream comprises less than 3 wt.-% of water such as, for example, from 1 to 2 wt.-% of water. The temperature of the top steam is preferably in the range of from 90 to 130° C., more preferably of from 95 to 120° C. and especially preferably of from 100 to 110° C.

The bottoms stream obtained from K41 has a preferred temperature of from 100 to 140° C., more preferably in the range of from 110 to 130° C. This bottoms stream is preferably fed into K42 and, prior to feeding, heated with the bottoms stream of K42 to a temperature of from 110 to 180° C., more preferably from 120 to 180° C., more preferably from 130 to 175° C. and still more preferably from 140 to 170° C. The bottoms stream obtained from K41 has a preferred methanol content of from 40 to 70 wt.-% and a preferred water content of from 30 to 60 wt.-%.

The top stream (M-vi1) obtained from column K42 comprises at least 85 wt.-% of methanol and up to 10 wt.-% of water, more preferably at least 90 wt.-% of methanol and up to 10 wt.-% of water, more preferably at least 95 wt.-% of methanol and up to 5 wt.-% of water, more preferably at least 96 wt.-% of methanol and up to 4 wt.-% of water, more preferably at least 97 wt.-% of methanol and up to 3 wt.-% of water, more preferably at least 98 wt.-% of methanol and up to 2 wt.-% of water, more preferably at least 98.5 wt.-% of methanol and up to 1.5 wt.-% of water, more preferably at least 98.5 wt.-% of methanol and up to 1 wt.-% of water.

The mixture (M-vi2) obtained from the bottom of column K42 comprises at least 90 wt.-% of water, more preferably at least 95 wt.-% of water and especially preferably at least 97 wt.-% of water. Preferably (M-dii) is essentially free of methanol, i.e. it has a methanol content of less than 0.5 wt.-%, preferably less than 5 ppm, more preferably of less than 1 ppm. In addition to water, (M-vi2) can comprise certain by-products resulting from one or more stages of the overall epoxidation process. Examples for such byproducts are glycol compounds such as propylene glycols. These by-products can be contained in (M-vi2) in an amount of up to 4 wt.-%, preferably up to 3 wt.-%.

According to the process of the present invention, it is possible that the mixture (M-v2) introduced into stage (vi) comprises by-products produced in at least one stage of the overall epoxidation process such as glycol ethers like methoxypropanols. As to these mixtures, it was surprisingly found that above-described two-pressure distillation, additionally comprising a dividing-wall column, allows for simultaneously separating these by-products from the methanol stream which is fed back as solvent into stage (a) and obtaining a mixture (M-vi2) as described above having a very low content regarding the by-products of not more than 4 wt.-%, preferably not more than 3 wt.-%.

A mixture (M-vi3) taken from the side-offtake of the dividing-wall column K42 comprises at least 10 wt.-% of glycol ethers, more preferably at least 15 wt.-% of glycol ethers and especially preferably at least 20 wt.-% of glycol ethers. Still more preferably, (M-diii) has a methanol content of not more than 5 wt.-%, more preferably less than 2 wt.-%, more preferably not more than 2 wt.-% and especially preferably less than 2 wt.-%.

As mentioned above, the top stream obtained either from the conventional distillation column K4 or from the dividing wall column K42, obtained as stream (M-vi2), is preferably recycled as methanol feed stream to stage (i) of the epoxidation process. Reference is made to the respective section "Methanol feed" hereinabove.

Further, it is conceivable to feed said stream (M-vi2) as external methanol reflux into the distillation column K2 used in stage (iv) as described above.

Therefore, the present invention also relates to above-described process, further comprising (vi) distilling the bottoms stream obtained from (v) in at least one distillation column K4 to obtain a bottoms stream having a methanol content of 0.5 wt.-% at most and a top stream having a methanol content of at least 98.5 wt.-% and a water content of 1 wt.-% at most;

(vii) recycling the top stream obtained from (vi) as starting material of the continuous epoxidation process.

The present invention is further illustrated by the following FIG. 1 and the Examples and Comparative Examples.

BRIEF DESCRIPTION OF THE FIGURE

FIG. 1 shows the by-product selectivities (in %) obtained from the examples and the comparative examples, plotted against the mean temperature T(mean) (in ° C.) of the cooling medium passed through the cooling jacket of reactor R1, as described in the Reference Example.

EXAMPLES

Reference Example

Catalyst Preparation and Process Set-Up

Propylene oxide was prepared in a main reactor R1 and a downstream reactor R2, separated by a distillation column K1. As catalyst in reactors R1 and R2, a titanium silicalite-1 catalyst was employed.

Preparation of the TS-1 Catalyst

| Powder Synthesis | | |
| --- | --- | --- |
| Starting materials: | 720 kg | tetraethoxy silane (TEOS) (Wacker, TES-28) |
| | 950 kg | tetra-n-propylammonium hydroxide (TPAOH) (40 wt.-% in water, Sachen, USA) |
| | 13.5 kg | tetraethoxy titanate (TEOT) (Du Pont, Tyzor ET) |

TEOS (300 kg) were loaded into a stirred tank reactor at room temperature and stirring (100 r.p.m.) was started. In a second vessel, 60 kg TEOS and 13.5 kg TEOT were first mixed and then added to the TEOS in the first vessel. Subsequently, another 360 kg TEOS were added to the mixture in the first vessel. Then, the content of the first vessel was stirred for 10 min before 950 g TPAOH were added. Stirring was continued for 60 min. Ethanol released by hydrolysis was separated by distillation at a bottoms temperature of 95° C. 300 kg water were then added to the content of the first vessel, and water in an amount equivalent to the amount of distillate was further added. The obtained mixture was stirred for 1 h. Crystallization was performed at 175° C. within 12 h at autogenous pressure. The obtained titanium silicalite-1 crystals were separated, dried, and calcined at a temperature of 500° C. in air for 6 h.

| Silica Sol Synthesis | | |
| --- | --- | --- |
| Starting materials: | 1096 kg | distilled water |
| | 760 kg | TEOS (Dynasil, Wacker) |
| | 2.5 liter | aqueous ammonia solution (25 wt.-%) |

In a vessel, 1096 g water were provided and 2.5 l aqueous ammonia solution were added. The obtained mixture was stirred for 15 min. Subsequently, the content of the vessel was heated to a temperature of 40° C. Then, 360 kg TEOS were added and the content of the vessel was heated to a temperature of 80° C. This temperature was maintained for 2 h (under reflux). Finally, the alcohol obtained by hydrolysis was distilled off by heating the content of the vessel to a temperature of 95° C. After distillation, the content of the vessel was cooled to a temperature of 40° C.

This procedure was repeated 4 times.

| Shaping | | |
| --- | --- | --- |
| Starting materials | 120 kg | TS-1 powder (obtained as described above) |
| | 40 kg | Aerosil 200 (Degussa) |
| | 176 kg | silica sol obtained as described above (22.5 wt.-% SiO$_2$) |
| | 8 kg | Walocel (Wolff, Walsrode, Germany) |
| | 4.9 kg | poly(ethylene oxide) (PEO) (Union Carbide, PolyOX Coagulant) |
| | 80 liter | distilled water |

TS-1 powder, Aerosil and Walocel were mixed for 20 min in a muller. Then, the silica sol was added. 35 min after the first addition of TS-1, 70 l of distilled water were added. After another 35 min, 2 kg PEO were added. After another 20 min, 10 l water were added. After another 10 min, 2.9 kg PEO were added. The formable mass was extruded through a matrix having circular holes with a diameter of 1.5 mm. The obtained strands were calcined in a band calciminer at a temperature of 550° C.

This procedure was repeated four times.

In total, 1740 kg strands were obtained with a bulk density of 470 to 480 g/l. The titanium content of the strands was 0.71 wt.-%, the Si content was 44 wt.-%. The pore volume of the strands, determined via Hg porosimetry, was 73 ml/g.

Reactor R1

The main reactor was a vertically arranged tubular reactor made of stainless steel with a length of 2000 mm and inner diameter of the tube of 28.5 mm. Through the tube, the reaction feed was passed from the bottom to the top, i.e. in upstream mode. Further, reactor R1 was equipped with a centered thermowell with an outer diameter of 8 mm extending from the bottom of the reaction tube to the top of the reaction tube. A 10-fold thermocouple with equally spaced thermoelements was placed in the thermowell allowing measurement of the temperature profile along the axis of the reaction tube. The pressure in reactor R1 was kept constant at 20 bar.

Reactor R1 was further equipped with a cooling jacket. As cooling medium, an ethyleneglycol/water mixture was passed through the cooling jacket in upstream mode. The flow rate of the cooling medium was adjusted so that the temperature difference between the inlet temperature and the outlet temperature of the cooling medium was 2° C. at most. Typically, this temperature difference was only about 0.5° C.

Reactor R1 further contained 620 g of strands of the heterogeneous titanium silicalite-1 catalyst prepared as described above. The length of the strands was in the range of from 3 to 5 mm. Empty space at the top of R1 was filled with glass beads having a diameter of 4 mm.

The reaction feed was obtained by mixing five individual streams:

A first stream (F1) which contained about 99 wt.-% of methanol and about 1 wt.-% of water. This stream was provided with a flow rate of 1700 g/h. This stream was free of potassium ions, free of sodium ions and free of phosphorus.

A second stream (F2), an aqueous hydrogen peroxide stream. This stream contained 40 wt.-% of hydrogen peroxide. As stabilizing agents, this hydrogen peroxide stream contained 98.6 micromol sodium ions per 1 mol hydrogen peroxide, 91.8 micromol phosphates (expressed as phosphorus, P) per 1 mol hydrogen peroxide, and 45 mg nitrate per kg of hydrogen peroxide. Apart from sodium, the hydrogen peroxide stream contained only traces (less than 10 wt.-ppb) of other metals (iron, aluminum, tin, palladium). Such aqueous hydrogen peroxide solution are commercially available, e.g. from Solvay as crude washed grade hydrogen peroxide prepared according to an anthraquinone process using a solvent system being essentially free of organic nitrogen and phosphorous compounds. This stream was provided with a flow rate of 278 g/h.

A third stream (F3), a propylene stream (polymer grade propylene) containing 99.9 wt.-% propene, the remainder essentially being propylene. This stream was provided with a flow rate of 142 g/h.

A fourth stream (F4) was an aqueous stream containing different hydrogenphosphate salts according to the inventive examples and comparative examples hereinunder. This fourth stream was added in an amount so that the individual molar ratios in the reaction feed according to the inventive examples and comparative examples hereinunder were obtained.

A fifth stream (F5, make-up MeOH) which results from the methanol recycling loop as described hereinunder was provided with a flow rate such that the methanol inventory in the plant remains constant.

All streams were provided with constant flow rates in liquid form, mixed, and the mixed stream, namely the reaction feed consisting of one single liquid phase, was passed into the reactor R1 at room temperature. Also the liquid reaction mixture in reactor R1 consisted of one single phase.

Every 20 minutes, the hydrogen peroxide content in the liquid fraction of the reactor effluent, obtained after depressurization of the reaction mixture, was automatically determined by colorimetry using a Metrohm ADI 2015 titrator combined with a Zeiss MCS521 diode array UV/vis spectrometer according to the titanylsulfate method. Based on this hydrogen peroxide content and the mass flows of the streams through R1, the hydrogen peroxide conversion was calculated. The temperature of the cooling medium passed through the cooling jacket of R1 as discussed above was adjusted so that the value of the hydrogen peroxide conversion thus determined was kept constant at a value of about 90%, i.e. in the range of from about 87 to about 93%.

Distillation Column K1

The reactor effluent from R1, the liquid and also the gaseous portion thereof, were passed to a distillation column and distilled at ambient pressure. The distillation column (DN25×2600 mm length, PN 10) was made of stainless steel and equipped with a Sulzer CY packing. The distillation was operated under ambient pressure and other operating conditions (heating of the bottoms, reflux ratio) were adjusted so that essentially all of the propylene oxide was contained in the top stream. The bottoms stream contained about 85 wt.-% of methanol and essentially all of the non-reacted hydrogen peroxide.

This bottoms stream was passed through a heat exchanger and brought to a temperature of 35° C. Before this stream was introduced into reactor R2, it was admixed with a propylene stream (polymer grade propylene containing 99.9 wt.-% propene, the remainder essentially being propane; flow rate: of 22.5 g/h).

Reactor R2

Reactor R2 was identical to R1 but operated as an essentially adiabatic reactor. R2 contained 292 g of the same titanium silicalite-1 catalyst as used in R1. To achieve adiabatic conditions, the jacket of R2 was evacuated, and R2 was additionally insulated. Contrary to the thermocouple used in R1, R2 contained a 5-fold thermocouple. As R1, R2 was operated in upstream mode wherein the pressure was adjusted to a value of 15 bar so that no gaseous phase was formed in R2. The hydrogen peroxide conversion in R2 was determined as described for R1. At the outlet of R2, the hydrogen peroxide conversion was at least 99.8%.

Further Processing of the Stream Exiting R2

The reaction mixture stream removed from R2 and the top stream obtained from K1 were combined and passed as feed stream to a downstream distillation column K2. K2 was made of stainless steel (DN25×3600 mm length, PN 10), equipped with a Sulzer CY packing and operated at ambient pressure. The distillation conditions (heating of the bottoms, external reflux ratio) were adjusted so that the propene content of the bottoms stream was below 100 wt.-ppm. Methanol having a temperature of 2° C. was used as external reflux and passed to the top of K2. The propylene oxide content of the top stream obtained from K2 was below 100 vol.-ppm. The bottoms stream obtained from K2 was then passed a downstream distillation column K3.

K3 was made of glass (DN50, 3300 mm length), equipped with a Sulzer EX packing and operated at ambient pressure. The distillation conditions (heating of the bottoms, reflux ratio) were adjusted so that the propylene oxide content of the bottoms stream was below 100 wt.-ppm. The propylene oxide content of the top stream obtained from K2 was at least 98 wt.-%. This top stream, a crude propylene oxide mixture, can be further purified or used as such, depending on the purity specifications. The bottoms stream obtained from K3 was then passed to a downstream distillation column K4.

K4 was made of glass (DN50, 2200 mm length), equipped with a Sulzer CY packing and operated at ambient pressure. The distillation conditions (heating of the bottoms, reflux ratio) were adjusted so that the bottoms stream has a methanol content of below 0.5 wt.-% and the top stream has a methanol content of at least 98.5 wt.-%, and a water content of 1 wt.-% at most. The major portion of this top stream is recycled as starting material into R1 (the first stream contained in the reaction feed, as described hereinabove); a minor portion of this top stream is used as external reflux for distillation column K2.

For determining the yields of the desired product propylene oxide, and of the byproducts 1-methoxy-2-propanol, 2-methoxy-1-propanol, propylene glycol, acetaldehyde, and oxygen, the amount and the composition of all the feed streams and exit streams were determined. To minimize the experimental errors all the liquid streams entering and leaving the plant were collected and their amount determined by weighing. The amount of the gaseous stream leaving at the top of distillation column K2 was determined by using a precision drum-type wet-test gas flow meters (Ritter, Series TG).

The composition of the liquid streams was determined by quantitative gas chromatography with an internal standard method. The water content was determined via Karl-Fischer titration. The hydrogen peroxide content of the aqueous solution employed as starting material was determined manganometrically The content of hydroperoxypropanols was indirectly determined via the propylene glycol content prior to and after reduction of said hydroperoxypropanols with triphenylphosphine. Since this by-product is only contained in internal streams, its determination is not relevant for determining the overall yields.

The composition of the gaseous stream was also determined by gas chromatography. All yields and selectivities are referred to hydrogen peroxide. Since the conversion of hydrogen peroxide is complete (hydrogen peroxide unconverted in R2 will decompose during work-up), the yield and the selectivity for a product are equal to each other. Since experiments are run for a long time and the apparatus used is in steady operation, the accumulation of reagents or products within the apparatus can be neglected. Mass balances over the period of the experiments agree within better than 2%.

The yield of a given product A based on hydrogen peroxide ($Y_A$) is generally determined by the general expression:

$$Y_A = n_A \times (\text{mol of product } A \text{ in exit streams})/(\text{mol of } H_2O_2 \text{ in feed stream } F2)$$

where
- $n_A$ is a stoichiometry factor defined as mols of $H_2O_2$ necessary to produce one mole of product A. This factor is 1 for propylene oxide, 1-methoxy-2-propanol, 2-methoxy-1-propanol and propylene glycol and 2 for oxygen and acetaldehyde which is formed by the acid catalyzed decomposition of the hydroperoxypropanols.
- "mol of product A in exit streams" as used in the equation above is defined as the total amount of product A contained in the all the streams exiting the plant during the time of the experiment expressed in mols.
- "mol of $H_2O_2$ in F2" as used in the equation above is defined as the total amount of $H_2O_2$ fed to the plant with stream F2 during the time of the experiment expressed in mols.

As indicated below, for carrying out the following experiments, reactors R1 and R2 were filled with fresh catalyst. Then, the methanol feed (F1) was started, and the plant was run as long as necessary to establish a stable methanol loop through reactor R1→bottoms of column K2→reactor R2→bottoms of column K2→bottoms of column K3→top of column K4 and back to the reactor R1. The temperature of the cooling medium passed through the cooling jacket of R1 was set to 29° C. and the temperature of the feed stream to R2 was set to 35° C. and kept constant throughout the experiments. Then, feeding of the hydrogen peroxide stream (F2), the propene stream (F3), the additive stream (F4), and the methanol make-up (F5) was started. If during an experiment, the catalyst deactivated, the temperature of the cooling medium in R1 was gradually increased in order to compensate this deactivation. Whether or not increasing the temperature of the cooling medium was necessary, was decided based on the hydrogen peroxide conversion determined as described above. Balancing was started once the hydrogen peroxide conversion in R1 reached the value of about 90% and was stable within the range from 87 to 93% and the entire plant was in steady state. After having conducted a given first experiment using a specific additive contained in the additive stream (F4), a given experiment using a different additive stream was conducted in most cases without changing the catalyst in R1 and R2. In order to minimize the difference in temperature between experiments, those with a larger amount of additive were run first and subsequent experiments with lesser amounts of additives. After changing the additive or its amount, the temperature of the cooling medium is adjusted to achieve the desired conversion of hydrogen peroxide in R1. Usually, less than 48 hours were necessary to achieve a new steady state after changing the amount and/or nature of the additive.

Example 1

Preparation of Propylene Oxide with a Potassium Content in the Reaction Feed of 133 Micromol per 1 mol Hydrogen Peroxide The experiment was performed with a fresh catalyst. Dipotassium hydrogen phosphate (1.25 wt.-%, aqueous solution) was added as stream F4. The amount of added dipotassium hydrogen phosphate solution was chosen so that in the reaction feed to R1, the molar ratio of potassium to hydrogen peroxide was 133 micromol K per mol hydrogen peroxide, the molar ratio of (potassium+sodium) to phosphorus was 1.46, the molar ratio of potassium to sodium was 1.35, and the molar ratio of potassium to phosphorus was 0.84. After having reached a constant hydrogen peroxide conversion of 90% in R1 (after 90 h, temperature of the cooling medium in R1 31.8° C.), the balance was started and continued for 250 h. In order to maintain the conversion of hydrogen peroxide in R1 constant the cooling medium in R1 had to be increased with an average rate of 0.35° C. per day. During the 250 h, the hydrogen peroxide conversion after R2, was 99.9%. The following yields were obtained:

| | |
|---|---|
| propylene oxide | 89.4% |
| 1-methoxy-2-propanol | 2.1% |
| 2-methoxy-1-propanol | 2.0% |
| propylene glycol | 0.8% |
| acetaldehyde | 1.1% |
| oxygen | 2.0% |

The total yield in 1-methoxy-2-propanol, 2-methoxy-1-propanol, propylene glycol, acetaldehyde, and oxygen was 8.0%. In this balance, several by-products being present in only minor amounts were not explicitly mentioned. This is why the above-mentioned yields do not add up to 100%. These by-products are, for example, dipropyleneglycol monomethylether, tripropyleneglycol monomethylether, dipropylene glycol, tripropylene glycol, formaldehyde, hydroxyacetone, propionaldehyde, acetone, methylformate, 1,1-dimethoxymethane, 1,1-dimethoxyethane, 1,1-dimethoxypropane, 4-methyl-1,3-dioxolane, 2,4-dimethyl-1,3-dioxolane, 2-ethyl-4-methyl-1,3-dioxolane, 2,2,4-trimethyl-1,3-dioxolane. If these by-products are taken into account, the error in the balance is <1%.

Comparative Example 1

Preparation of Propylene Oxide with a Potassium Content in the Reaction Feed of 100 Micromol per 1 mol Hydrogen Peroxide The experiment according to Example 1 was continued. Dipotassium hydrogen phosphate (1.25 wt.-%, aqueous solution) was added as stream F4. The amount of added dipotassium hydrogen phosphate solution was chosen so that in the reaction feed to R1, the molar ratio of potassium to hydrogen peroxide was 100 micromol K per mol hydrogen peroxide. The molar ratio of (potassium+sodium) to phosphorus was then 1.40, the molar ratio of potassium to sodium was 1.01, and the molar ratio of potassium to phosphorus was 0.70. After 40 h, a constant hydrogen peroxide conversion of 90% in R1 was reached, at a cooling medium temperature of 33.9° C. At this point, the balance was started and continued for 340 h. In order to maintain the conversion of hydrogen peroxide in R1 constant the cooling medium in R1 had to be increased with an average rate of 0.46° C. per day. During the 340 h, the hydrogen peroxide conversion, after R2, was 99.9%. The following yields were obtained:

| | |
|---|---|
| propylene oxide | 86.3% |
| 1-methoxy-2-propanol | 2.5% |
| 2-methoxy-1-propanol | 2.7% |

| propylene glycol | 1.1% |
| acetaldehyde | 1.4% |
| oxygen | 1.6% |

The total yield in 1-methoxy-2-propanol, 2-methoxy-1-propanol, propylene glycol, acetaldehyde, and oxygen was 9.3%. In this balance, several by-products being present in only minor amounts were not explicitly mentioned. Reference is made to the respective discussion in Example 1. If the by-products are taken into account, the error in balance is <1%.

Comparative Example 2

Preparation of Propylene Oxide with a Caesium Content in the Reaction Feed of 129 Micromol per 1 mol Hydrogen Peroxide The experiment according to Comparative Example 1 was continued. The additive contained in stream F4 was changed. Instead of dipotassium hydrogen phosphate, dicesium hydrogen phosphate (1.25 wt.-%, aqueous solution) was added as stream F4. The amount of added dicesium hydrogen phosphate solution was chosen so that in the reaction feed to R1, the molar ratio of caesium to hydrogen peroxide was 129 micromol Cs per mol hydrogen peroxide. The molar ratio of sodium to phosphorus was then 0.63, the molar ratio of potassium to sodium was 0, and the molar ratio of potassium to phosphorus was 0. After 38 h, a constant hydrogen peroxide conversion of 90% in R1 was reached, at a cooling medium temperature of 41.1° C. At this point, the balance was started and continued for 140 h. In order to maintain the conversion of hydrogen peroxide in R1 constant the cooling medium in R1 had to be increased with an average rate of 0.25° C. per day. During the 140 h, the hydrogen peroxide conversion, after R2, was 99.9%. The following yields were obtained:

| propylene oxide | 86.5% |
| 1-methoxy-2-propanol | 2.0% |
| 2-methoxy-1-propanol | 1.8% |
| propylene glycol | 0.8% |
| acetaldehyde | 1.1% |
| oxygen | 4.4% |

The total yield in 1-methoxy-2-propanol, 2-methoxy-1-propanol, propylene glycol, acetaldehyde, and oxygen was 10.1%. In this balance, several by-products being present in only minor amounts were not explicitly mentioned. Reference is made to the respective discussion in Example 1. If the by-products are taken into account, the error in balance is <1%.

Comparative Example 3

Preparation of Propylene Oxide with a Sodium Content in the Reaction Feed of 270.6 Micromol per 1 mol Hydrogen Peroxide The experiment was performed with a fresh catalyst, as in Example 1. Disodium hydrogen phosphate (1.25 wt.-%, aqueous solution) was added as stream F4. The amount of added disodium hydrogen phosphate solution was chosen so that in the reaction feed to R1, the molar ratio of sodium to hydrogen peroxide was 270.6 micromol Na per mol hydrogen peroxide (i.e. in addition to the sodium contained in the stream F2, 98.6 micromol Na per mol hydrogen peroxide, another 172 micromol sodium per 1 mol hydrogen peroxide were added via stream F4). The molar ratio of sodium to phosphorus was then 1.52, the molar ratio of potassium to sodium was 0, and the molar ratio of potassium to phosphorus was 0. After having reached a constant hydrogen peroxide conversion of 90% in R1 (after 120 h, temperature of the cooling medium 31.0° C.), the balance was started and continued for 260 h. In order to maintain the conversion of hydrogen peroxide in R1 constant the cooling medium in R1 had to be increased with an average rate of 0.31° C. per day. During the 260 h, the hydrogen peroxide conversion, after R2, was 99.85%. The following yields were obtained:

| propylene oxide | 89.0% |
| 1-methoxy-2-propanol | 2.0% |
| 2-methoxy-1-propanol | 1.9% |
| propylene glycol | 0.8% |
| acetaldehyde | 1.3% |
| oxygen | 3.1% |

The total yield in 1-methoxy-2-propanol, 2-methoxy-1-propanol, propylene glycol, acetaldehyde, and oxygen was 9.1%. In this balance, several by-products being present in only minor amounts were not explicitly mentioned. Reference is made to the respective discussion in Example 1. If the by-products are taken into account, the error in balance is <1%.

Comparative Example 4

Preparation of Propylene Oxide with a Potassium Content in the Reaction Feed of 195 Micromol Per 1 Mol Hydrogen Peroxide The experiment according to Comparative Example 3 was continued. Dipotassium hydrogen phosphate (1.25 wt.-%, aqueous solution) was added as stream F4. The amount of added dipotassium hydrogen phosphate solution was chosen so that in the reaction feed to R1, the molar ratio of potassium to hydrogen peroxide was 195 micromol K per mol hydrogen peroxide. The molar ratio of (potassium+sodium) to phosphorus was then 1.55, the molar ratio of potassium to sodium was 1.98, and the molar ratio of potassium to phosphorus was 1.03. After 10 h, a constant hydrogen peroxide conversion of 90% in R1 was reached, at a cooling medium temperature of 38.0° C. At this point, the balance was started and continued for 180 h. In order to maintain the conversion of hydrogen peroxide in R1 constant the cooling medium in R1 had to be increased with an average rate of 0.31° C. per day. During the 180 h, the hydrogen peroxide conversion, after R2, was 99.85%. The following yields were obtained:

| propylene oxide | 88.0% |
| 1-methoxy-2-propanol | 1.9% |
| 2-methoxy-1-propanol | 1.4% |
| propylene glycol | 0.8% |
| acetaldehyde | 1.4% |
| oxygen | 3.3% |

The total yield in 1-methoxy-2-propanol, 2-methoxy-1-propanol, propylene glycol, acetaldehyde, and oxygen was 8.8%. In this balance, several by-products being present in only minor amounts were not explicitly mentioned. Reference is made to the respective discussion in Example 1. If the by-products are taken into account, the error in balance is <1%.

Example 2

Preparation of Propylene Oxide with a Potassium Content in the Reaction Feed of 155 Micromol Per 1 Mol Hydrogen Peroxide The experiment according to Comparative Example 4 was continued. Dipotassium hydrogen phosphate (1.25 wt.-%, aqueous solution) was added as stream F4. The amount of added dipotassium hydrogen phosphate solution was chosen so that in the reaction feed to R1, the molar ratio of potassium to hydrogen peroxide was 155 micromol K per mol hydrogen peroxide. The molar ratio of (potassium+sodium) to phosphorus was then 1.50, the molar ratio of potassium to sodium was 1.57, and the molar ratio of potassium to phosphorus was 0.91. After 110 h, a constant hydrogen peroxide conversion of 90% in R1 was reached, at a cooling medium temperature of 38.0° C. At this point, the balance was started and continued for 170 h. In order to maintain the conversion of hydrogen peroxide in R1 constant the cooling medium in R1 had to be increased with an average rate of 0.31° C. per day. During the 170 h, the hydrogen peroxide conversion, after R2, was 99.85%. The following yields were obtained:

| | |
|---|---|
| propylene oxide | 88.5% |
| 1-methoxy-2-propanol | 2.0% |
| 2-methoxy-1-propanol | 1.5% |
| propylene glycol | 0.8% |
| acetaldehyde | 1.1% |
| oxygen | 2.6% |

The total yield in 1-methoxy-2-propanol, 2-methoxy-1-propanol, propylene glycol, acetaldehyde, and oxygen was 8.0%. In this balance, several by-products being present in only minor amounts were not explicitly mentioned. Reference is made to the respective discussion in Example 1. If the by-products are taken into account, the error in balance is <1%.

Comparative Example 5

Preparation of Propylene Oxide with a Sodium Content in the Reaction Feed of 198.6 Micromol Per 1 Mol Hydrogen Peroxide The experiment was performed with a fresh catalyst, as in Example 1. Disodium hydrogen phosphate (1.25 wt.-%, aqueous solution) was added as stream F4. The amount of added disodium hydrogen phosphate solution was chosen so that in the reaction feed to R1, the molar ratio of sodium to hydrogen peroxide was 198.6 micromol Na per mol hydrogen peroxide (i.e. in addition to the sodium contained in stream F2, 98.6 micromol Na per mol hydrogen peroxide, another 100 micromol sodium per 1 mol hydrogen peroxide were added via stream F4). The molar ratio of sodium to phosphorus was then 1.40, the molar ratio of potassium to sodium was 0, and the molar ratio of potassium to phosphorus was 0. After having reached a constant hydrogen peroxide conversion of 90% in R1 (after 120 h, temperature of the cooling medium 29.5° C.), the balance was started and continued for 230 h. In order to maintain the conversion of hydrogen peroxide in R1 constant the cooling medium in R1 had to be increased with an average rate of 0.64° C. per day. During the 230 h, the hydrogen peroxide conversion, after R2, was 99.8%. The following yields were obtained:

| | |
|---|---|
| propylene oxide | 86.6% |
| 1-methoxy-2-propanol | 2.8% |
| 2-methoxy-1-propanol | 3.2% |
| propylene glycol | 1.2% |
| acetaldehyde | 1.2% |
| oxygen | 1.5% |

The total yield in 1-methoxy-2-propanol, 2-methoxy-1-propanol, propylene glycol, acetaldehyde, and oxygen was 9.9%. In this balance, several by-products being present in only minor amounts were not explicitly mentioned. Reference is made to the respective discussion in Example 1. If the by-products are taken into account, the error in balance is <1%.

Comparative Example 6

Preparation of Propylene Oxide with an Ammonium Content in the Reaction Feed of 171 Micromol Per 1 Mol Hydrogen Peroxide The experiment was performed with a fresh catalyst, as in Example 1. Diammonium hydrogen phosphate (1.25 wt.-%, aqueous solution) was added as stream F4. The amount of added diammonium hydrogen phosphate solution was chosen so that in the reaction feed to R1, the molar ratio of ammonium to hydrogen peroxide was 171 micromol ammonium per mol hydrogen peroxide (since no ammonium is contained in stream F2, all of the ammonium is added via stream F4). The molar ratio of sodium to phosphorus was then 0.56, the molar ratio of potassium to sodium was 0, and the molar ratio of potassium to phosphorus was 0. After having reached a constant hydrogen peroxide conversion of 90% in R1 (after 100 h, temperature of the cooling medium 29.3° C.), the balance was started and continued for 216 h. In order to maintain the conversion of hydrogen peroxide in R1 constant the cooling medium in R1 had to be increased with an average rate of 1.1° C. per day. During the 216 h, the hydrogen peroxide conversion, after R2, was 99.9%. The following yields were obtained:

| | |
|---|---|
| propylene oxide | 86.9% |
| 1-methoxy-2-propanol | 3.1% |
| 2-methoxy-1-propanol | 3.9% |
| propylene glycol | 1.3% |
| acetaldehyde | 0.7% |
| oxygen | 0.7% |

The total yield in 1-methoxy-2-propanol, 2-methoxy-1-propanol, propylene glycol, acetaldehyde, and oxygen was 9.7%. In this balance, several by-products being present in only minor amounts were not explicitly mentioned. Reference is made to the respective discussion in Example 1. If the by-products are taken into account, the error in balance is <1%.

Summary of the Examples and Comparative Examples

| Example | Additiv M | Added amount of M (micromol/ mol $H_2O_2$) | Potassium in the reaction feed (micromol/ mol $H_2O_2$) | K/P in the reaction feed (mol/mol) | (Na + K)/P in the reaction feed (mol/mol) | K/Na in the reaction feed (mol/mol) | T (mean) (°C.)[b] | By-product yield (%)[a] |
|---|---|---|---|---|---|---|---|---|
| E 1  | Potassium | 133 | 133 | 0.84 | 1.46 | 1.35 | 33.6 | 8.0 |
| CE 1 | Potassium | 100 | 100 | 0.70 | 1.40 | 1.01 | 37.2 | 9.3 |
| CE 2 | Cesium    | 129 | 0   | 0    | 0.63 | 0    | 41.8 | 10.1 |
| CE 3 | Sodium    | 172 | 0   | 0    | 1.52 | 0    | 32.7 | 9.1 |
| CE 4 | Potassium | 195 | 195 | 1.03 | 1.55 | 1.98 | 39.2 | 8.8 |
| E 2  | Potassium | 155 | 155 | 0.91 | 1.50 | 1.57 | 39.1 | 8.0 |
| CE 5 | Sodium    | 100 | 0   | 0    | 1.40 | 0    | 32.6 | 9.9 |
| CE 6 | Ammonium  | 171 | 0   | 0    | 0.56 | 0    | 31.9 | 9.7 |

[a] Sum of the yields of 1-methoxy-2-propanol, 2-methoxy-1-propanol, propylene glycol, acetal-dehyde and oxygen. The yield is calculated relative to hydrogen peroxide.
[b] T (mean) is defined as (temperature of cooling medium in R1 at the beginning of the balance + temperature of cooling medium in R1 at the end of the balance)/2

Comparison of the examples wherein potassium is added
(arranged according to increasing amount of added potassium)

| Example | Additiv M | Added amount of M (micromol/ mol $H_2O_2$) | Potassium in the reaction feed (micromol/ mol $H_2O_2$) | K/P in the reaction feed (mol/mol) | (Na + K)/P in the reaction feed (mol/mol) | K/Na in the reaction feed (mol/mol) | T (mean) (°C.) | By-product yield (%) |
|---|---|---|---|---|---|---|---|---|
| CE 1 | Potassium | 100 | 100 | 0.70 | 1.40 | 1.01 | 37.2 | 9.3 |
| E 1  | Potassium | 133 | 133 | 0.84 | 1.46 | 1.35 | 33.6 | 8.0 |
| E 2  | Potassium | 155 | 155 | 0.91 | 1.50 | 1.57 | 39.1 | 8.0 |
| CE 4 | Potassium | 195 | 195 | 1.03 | 1.55 | 1.98 | 39.2 | 8.8 |

This comparison shows that only above 100 micromol and below 195 micromol of added potassium, a preferred low by-product selectivity was obtained. Therefore, it was shown that there is a preferred range for potassium contained in the reaction feed which reads to a low by-product selectivity.

Comparison of the examples regarding replacing potassium by cesium

| Example | Additiv M | Added amount of M (micromol/ mol $H_2O_2$) | Potassium in the reaction feed (micromol/ mol $H_2O_2$) | K/P in the reaction feed (mol/mol) | (Na + K)/P in the reaction feed (mol/mol) | K/Na in the reaction feed (mol/mol) | T (mean) (°C.) | By-product yield (%) |
|---|---|---|---|---|---|---|---|---|
| E 1  | Potassium | 133 | 133 | 0.84 | 1.46 | 1.35 | 33.6 | 8.0 |
| CE 2 | Cesium    | 129 | 0   | 0    | 0.63 | 0    | 41.8 | 10.1 |

The comparison of Example 1 and Comparative Example 2 shows that while the amount of added M is essentially constant, replacing potassium by essentially the same amount of cesium—leading to ratios of K/$H_2O_2$, K/P, (Na+K)/P and K/Na in the reaction feed which are outside the inventive, preferred ranges—leads to a clearly increased by-product selectivity.

Comparison of the examples regarding replacing potassium by sodium

| Example | Additiv M | Added amount of M (micromol/mol $H_2O_2$) | Potassium in the reaction feed (micromol/mol $H_2O_2$) | K/P in the reaction feed (mol/mol) | (Na + K)/P in the reaction feed (mol/mol) | K/Na in the reaction feed (mol/mol) | T (mean) (° C.) | By-product yield (%) |
|---|---|---|---|---|---|---|---|---|
| CE 3 | Sodium | 172 | 0 | 0 | 1.52 | 0 | 32.7 | 9.1 |
| E 2 | Potassium | 155 | 155 | 0.91 | 1.50 | 1.57 | 39.1 | 8.0 |
| CE 1 | Potassium | 100 | 100 | 0.70 | 1.40 | 1.01 | 37.2 | 9.3 |
| CE 5 | Sodium | 100 | 0 | 0 | 1.40 | 0 | 32.6 | 9.9 |

The comparison of Comparative Example 3 with Example 2, both having a similar amount of added M, shows that replacing potassium by sodium leads to an increased by-product selectivity. Moreover, this comparison shows that it is not only the (Na+K)/P ratio which leads to low by-product selectivities (both values are in the preferred range); necessarily, the additive M has to be potassium in order to achieve the preferred results.

Although Comparative Example 1 shows an amount of added potassium which is outside the inventive range, the comparison of CE 1 with CE 5 nevertheless shows that as far as potassium and sodium are concerned, potassium is the preferred additive.

Comparison of the examples regarding replacing potassium by ammonium

| Example | Additiv M | Added amount of M (micromol/mol $H_2O_2$) | Potassium in the reaction feed (micromol/mol $H_2O_2$) | K/P in the reaction feed (mol/mol) | (Na + K)/P in the reaction feed (mol/mol) | K/Na in the reaction feed (mol/mol) | T (mean) (° C.) | By-product yield (%) |
|---|---|---|---|---|---|---|---|---|
| CE 3 | Sodium | 172 | 0 | 0 | 1.52 | 0 | 32.7 | 9.1 |
| E 2 | Potassium | 155 | 155 | 0.91 | 1.50 | 1.57 | 39.1 | 8.0 |
| CE 6 | Ammonium | 171 | 0 | 0 | 0.56 | 0 | 31.9 | 9.7 |

The comparison of Comparative Examples 3 and 6 (and Example 2) shows that replacing non-preferred sodium by essentially the same amount of ammonium leads to an even more increased by-product selectivity. Reference is also made to the comparison of sodium with potassium above. As discussed above, all balance experiments were performed at a constant value of hydrogen peroxide conversion of 90% in reactor R1. In order to show that the by-product selectivities obtained from the examples and comparative examples are not correlated with T(mean)—the mean temperatures being within a comparatively narrow range of about 10° C.—reference is made to FIG. 1. There, the by-product selectivities (in %) are plotted against T(mean) (in ° C.). This proves that choosing a constant value of hydrogen peroxide conversion as reference point is the best choice, all the more as it is known that it is this conversion which has a significant influence on the by-product selectivities because the reactions leading to the by-products are essentially consecutive reactions.

CITED REFERENCES

Clerici et al., J. Catal. 140 (1993) pages 71-83
EP 0 230 949 A2
EP 0 712 852 A1
EP 0 757 043 A1
WO 99/48882 A1
WO 2004/029032 A1
EP 1 085 017 A1
EP 1 122 249 A1
Ullmann's Encyclopedia of Industrial Chemistry, 5$^{th}$ edition, volume A13 (1989) pages 443-466
Ullmann's Encyclopedia of Industrial Chemistry, 5$^{th}$ Edition, Volume A22, page 214
WO 2005/103024 A1
WO 2010/130610 A1
WO 2007/074101 A1

The present invention includes the following embodiments, wherein these embodiments include the specific combinations of embodiments as indicated by the respective interdependencies defined therein:

1. A continuous process for the production of propylene oxide comprising reacting propene with hydrogen peroxide in methanolic solution in the presence of a titanium silicalite-1 catalyst to obtain propylene oxide, wherein a reaction feed comprising propene, methanol and hydrogen peroxide is introduced into a reactor, said reaction feed containing potassium cations ($K^+$) in an amount of from 110 to 190 micromol, relative to 1 mol hydrogen peroxide contained in the reaction feed, and further containing phosphorus (P) in the form of anions of at least one phosphorus oxyacid.
2. The process of embodiment 1, wherein the reaction feed contains $K^+$ in an amount of from 120 to 175 micromol, preferably of from 130 to 160 micromol, relative to 1 mol hydrogen peroxide contained the reaction feed.
3. The process of embodiment 1 or 2, wherein in the reaction feed, the molar ratio of $K^+$ relative to P is in the range of from 0.75 to 1.0, preferably of from 0.8 to 0.95.
4. The process of any of embodiments 1 to 3, wherein the reaction feed additionally contains sodium ions ($Na^+$).

5. The process of embodiment 4, wherein in the reaction feed, the molar ratio of $K^+$ relative to $Na^+$ is greater than or equal to 0.1.

6. The process of embodiment 4 or 5, wherein in the reaction feed, the molar ratio of $K^+$ relative to $Na^+$ is in the range of from 1.0 to 3.0, preferably from 1.2 to 1.75, more preferably of from 1.3 to 1.6.

7. The process of any of embodiments 4 to 6, wherein in the reaction feed, the molar ratio of $K^+$ plus $Na^+$ relative to P is in the range of from 1.43 to 1.53, preferably from 1.44 to 1.52, more preferably of from 1.45 to 1.51.

8. The process of any of embodiments 1 to 7, wherein the total amount of (a) alkali metal ions other than $K^+$ and $Na^+$, (b) alkaline earth metal ions, and (c) other metal ions contained in the reaction feed is 5 micromol at most, preferably of 3 micromol at most, more preferably of 1 micromol at most, relative to 1 mol hydrogen peroxide contained the reaction feed.

9. The process of any of embodiments 1 to 8, wherein the reaction feed is obtained from a hydrogen peroxide feed, a methanol feed, and a propene feed.

10. The process of embodiment 9, wherein the hydrogen peroxide feed contains $K^+$ in an amount of less than 110 micromol, preferably less than 70 micromol, more preferably less than 30 micromol, in particular less than 5 micromol, relative to 1 mol hydrogen peroxide contained in the hydrogen peroxide feed.

11. The process of embodiment 10, wherein at least one solution containing $K^+$ and P in the form of anions of at least one phosphorus oxyacid is added to the hydrogen peroxide feed or to the propene feed or to the methanol feed or a mixed feed of two or three thereof, in such an amount that the reaction feed contains K+, Na+, and P in the form of anions of at least one phosphorus oxyacid in amounts as defined in any of embodiments 1 to 7.

12. The process of embodiment 11, wherein the at least one solution is an aqueous solution of dipotassium hydrogen phosphate.

13. The process of any of embodiments 9 to 12, wherein the hydrogen peroxide feed is an aqueous or a methanolic or an aqueous/methanolic, preferably an aqueous hydrogen peroxide feed, containing hydrogen peroxide preferably in an amount of from 25 to 75 wt.-%, more preferably of from 30 to 50 wt.-%.

14. The process of any of embodiments 9 to 13, wherein the propene feed additionally contains propane wherein the volume ratio of propene to propane is preferably in the range of from 99.99:0.01 to 95:5.

15. The process of any of embodiments 1 to 14, wherein the reaction feed when introduced into the reactor consists of one liquid phase.

16. The process of any of embodiments 1 to 15, wherein the pressure under which the reaction of propene with hydrogen peroxide in methanolic solution in the presence of the titanium silicalite-1 catalyst is carried out in the reactor is at least 10 bar, preferably at least 15 bar, more preferably at least 20 bar and in particular in the range of from 20 to 40 bar.

17. The process of any of embodiments 1 to 16, wherein the reaction mixture in the reactor is externally and/or internally cooled such that the maximum temperature of the reaction mixture in the reactor is in the range of from 30 to 70° C.

18. The process of any of embodiments 1 to 17, wherein the titanium silicalite-1 catalyst contains titanium silicalite-1 as catalytically active material embedded in a porous matrix, preferably in a mesoporous matrix, more preferably in a mesoporous silica matrix.

19. The process of any of embodiments 1 to 18, wherein the reaction of propene with hydrogen peroxide in methanolic solution in the presence of the titanium silicalite-1 catalyst is carried out by a method comprising
(i) reacting propene with hydrogen peroxide in methanolic solution in the presence of the titanium silicalite-1 catalyst in at least one reactor R1 which is preferably operated in isothermal mode, wherein a reaction feed comprising propene, methanol and hydrogen peroxide is introduced into R1, said reaction feed containing potassium cations ($K^+$) in an amount of from 110 to 190 micromol, relative to 1 mol hydrogen peroxide contained the reaction feed, and further containing phosphorus (P) in the form of anions of at least one phosphorus oxyacid;
(ii) separating a stream containing non-reacted hydrogen peroxide from the reaction mixture obtained from (i) and removed from R1, said separating preferably being carried out by distillation in at least 1, preferably 1 distillation column K1;
(iii) mixing the stream containing non-reacted hydrogen peroxide with a propene stream, passing the mixed stream into at least 1, preferably 1 reactor R2 containing the titanium silicalite-1 catalyst and preferably being operated in adiabatic mode, and reacting propene with hydrogen peroxide in R2,
wherein the hydrogen peroxide conversion in R1 is preferably in the range of from 85 to 95%, more preferably in the range of from 87 to 93%.

20. The process of embodiment 19, further comprising
(iv) distilling a combined stream consisting of the reaction mixture obtained from (iii) and removed from R2, and the top stream obtained from K1, in a distillation column K2 to obtain a top stream having a propylene oxide content of 100 vol.-ppm at most and a bottoms stream having a propene content of 100 wt.-ppm at most, said distilling preferably being carried out using a methanol stream as external reflux;
(v) distilling the bottoms stream obtained from (iv) in a distillation column K3 to obtain a top stream mixture containing at least 98 wt.-% of propylene oxide and a bottoms stream having a propylene oxide content of 100 wt.-ppm at most.

21. The process of embodiment 20, further comprising
(vi) distilling the bottoms stream obtained from (v) in at least one distillation column K4 to obtain a bottoms stream having a methanol content of 0.5 wt.-% at most and a top stream having a methanol content of at least 98.5 wt.-% and a water content of 1 wt.-% at most;
(vii) recycling the bottoms stream obtained from (vi) as starting material of the continuous process according to any of embodiments 1 to 20 and/or as external reflux into (iv) according to embodiment 20.

22. A process for the preparation of hydrogen peroxide, comprising
preparing a reaction mixture via an anthrachinone process;
preparing a crude hydrogen peroxide solution by subjecting the reaction mixture to an extraction stage using water, preferably essentially pure water as extracting agent, said crude hydrogen peroxide solution having a $K^+$ content of less than 110 micromol;
optionally subjecting the crude hydrogen peroxide solution to a further extraction stage to obtain a crude washed hydrogen peroxide solution;

adding a solution containing K⁺, preferably containing K⁺ and P in the form of anions of at least one phosphorus oxyacid, to the crude hydrogen peroxide solution or to the crude washed hydrogen peroxide solution.

23. A mixture containing at least 99.99 wt.-% of propylene oxide, comprising less than 3 wt.-ppm acetaldehyde, preferably being free of acetaldehyde.

24. The mixture of embodiment 23, obtainable or obtained by a process according to embodiment 20 as top stream mixture in (v).

The invention claimed is:

1. A continuous process for the production of propylene oxide comprising:
reacting propene with hydrogen peroxide in a methanolic solution in the presence of a titanium silicalite-1 catalyst to obtain propylene oxide,
wherein a reaction feed comprising propene, methanol and hydrogen peroxide is introduced into a reactor, wherein the reaction feed comprises from 110 to 190 micromol of potassium cations (K⁺), relative to 1 mol hydrogen peroxide contained in the reaction feed, and
wherein the reaction feed further comprises phosphorus (P) in the form of anions of at least one phosphorus oxyacid.

2. The process of claim 1, wherein the reaction feed comprises from 120 to 175 micromol of K⁺, relative to 1 mol hydrogen peroxide contained the reaction feed.

3. The process of claim 1, wherein in the reaction feed, a molar ratio of K⁺ to P is from 0.75 to 1.0.

4. The process of claim 1, wherein the reaction feed additionally comprises sodium ions (Na⁺).

5. The process of claim 4, wherein in the reaction feed, a molar ratio of K⁺ to Na⁺ at least 0.1.

6. The process of claim 4, wherein in the reaction feed, a molar ratio of K⁺ to Na⁺ is from 1.0 to 3.0.

7. The process of claim 4, wherein in the reaction feed, a molar ratio of K⁺ plus Na⁺ to P is from 1.43 to 1.53.

8. The process of claim 1, wherein the total amount of (a) alkali metal ions other than K⁺ and Na⁺, (b) alkaline earth metal ions, and (c) other metal ions contained in the reaction feed is 5 micromol at most, relative to 1 mol hydrogen peroxide contained the reaction feed.

9. The process of claim 1, wherein the reaction feed is obtained from a hydrogen peroxide feed, a methanol feed, and a propene feed.

10. The process of claim 9, wherein the hydrogen peroxide feed contains less than 110 micromol of K⁺, relative to 1 mol hydrogen peroxide contained in the hydrogen peroxide feed.

11. The process of claim 10, wherein at least one solution containing K⁺ and P in the form of anions of at least one phosphorus oxyacid is added to at least one feed selected form the group consisting of the hydrogen peroxide feed, the propene feed, and the methanol feed, in such an amount that the reaction feed contains K+, Na+, and P in the form of anions of at least one phosphorus oxyacid in amounts as defined in claim 1.

12. The process of claim 11, wherein the at least one solution is an aqueous solution of dipotassium hydrogen phosphate.

13. The process of claim 9, wherein the hydrogen peroxide feed is an aqueous or a methanolic or an aqueous/methanolic.

14. The process of claim 9, wherein the propene feed additionally comprises propane.

15. The process of claim 1, wherein the reaction feed when introduced into the reactor consists of one liquid phase.

16. The process of claim 1, wherein the pressure under which the reaction of propene with hydrogen peroxide in the methanolic solution in the presence of the titanium silicalite-1 catalyst is carried out in the reactor is at least 10 bar.

17. The process of claim 1, wherein the reaction mixture in the reactor is externally and/or internally cooled, wherein the maximum temperature of the reaction mixture in the reactor from 30 to 70° C.

18. The process of claim 1, wherein the titanium silicalite-1 catalyst contains titanium silicalite-1 as a catalytically active material embedded into a porous matrix.

19. The process of claim 1, wherein the reaction of propene with hydrogen peroxide in the methanolic solution in the presence of the titanium silicalite-1 catalyst is carried out by a method comprising:
(i) reacting propene with hydrogen peroxide in the methanolic solution in the presence of the titanium silicalite-1 catalyst in at least one reactor R1, wherein a reaction feed comprising propene, methanol and hydrogen peroxide is introduced into R1, wherein the reaction feed comprises from 110 to 190 micromol of potassium cations (K⁺), relative to 1 mol hydrogen peroxide contained the reaction feed, and further comprises phosphorus (P) in the form of anions of at least one phosphorus oxyacid;
(ii) separating a stream containing non-reacted hydrogen peroxide from the reaction mixture obtained from (i) and removed from R1, wherein the separating is carried out by distillation in at least 1 distillation column K1; and
(iii) mixing the stream containing non-reacted hydrogen peroxide with a propene stream, passing the mixed stream into at least 1 reactor R2 containing the titanium silicalite-1 catalyst, and reacting propene with hydrogen peroxide in R2.

20. The process of claim 19, further comprising:
(iv) distilling a combined stream comprising the reaction mixture obtained from (iii) and removed from R2, and the top stream obtained from K1, in a distillation column K2 to obtain a top stream having a propylene oxide content of not greater than 100 vol. ppm and a bottom stream having a propene content of not greater than 100 wt. ppm;
(v) distilling the bottoms stream obtained from (iv) in a distillation column K3 to obtain a top stream mixture comprising at least 98 wt. % of propylene oxide and a bottom stream having a propylene oxide content of not greater than 100 wt. ppm.

21. The process of claim 20, further comprising:
(vi) distilling the bottom stream obtained from (v) in at least one distillation column K4 to obtain a bottoms stream having a methanol content of not greater than 0.5 wt. % and a top stream having a methanol content of at least 98.5 wt. % and a water content of not greater than 1 wt. %;
(vii) recycling the bottoms stream obtained from (vi) as a starting material of the continuous process according to claim 1 and/or as external reflux into (iv) according to claim 20.

* * * * *